United States Patent
Hegde et al.

(10) Patent No.: US 10,485,714 B2
(45) Date of Patent: Nov. 26, 2019

(54) ABSORBENT ARTICLE WITH CUSHION LAYER DEFINING AIR POCKETS

(71) Applicant: ASSOCIATED HYGIENIC PRODUCTS, LLC, Greenville, SC (US)

(72) Inventors: Raghavendra R. Hegde, Marion, OH (US); Trent Ottery, Delaware, OH (US); Steve Linton, Wilmington, NC (US)

(73) Assignee: ASSOCIATED HYGIENIC PRODUCTS, LLC, Greenville, SC (US)

( * ) Notice: Subject to any disclaimer, the term of this patent is extended or adjusted under 35 U.S.C. 154(b) by 616 days.

(21) Appl. No.: 14/969,981

(22) Filed: Dec. 15, 2015

(65) Prior Publication Data

US 2016/0193091 A1    Jul. 7, 2016

Related U.S. Application Data

(60) Provisional application No. 62/091,929, filed on Dec. 15, 2014.

(51) Int. Cl.
*A61F 13/15* (2006.01)
*A61F 13/534* (2006.01)
(Continued)

(52) U.S. Cl.
CPC ...... *A61F 13/534* (2013.01); *A61F 13/15699* (2013.01); *B32B 3/00* (2013.01); *B32B 3/04* (2013.01); *B32B 3/12* (2013.01); *B32B 3/28* (2013.01); *B32B 3/30* (2013.01); *B32B 5/022* (2013.01); *B32B 5/08* (2013.01);
(Continued)

(58) Field of Classification Search
CPC .............. A61F 13/534; A61F 13/15699; A61F 2013/15024; A61F 2013/530226; A61F 2013/530489; A61F 2013/53081; B32B 4/18; B32B 7/12; B32B 27/065; B32B 27/08; B32B 27/10; B32B 27/12; B32B 29/002; B32B 29/08; B32B 33/00; B32B 37/14; B32B 37/12; B32B 37/1292; B32B 2266/025; B32B 2266/0278;
(Continued)

(56) References Cited

U.S. PATENT DOCUMENTS

| 3,468,311 A | 9/1969 | Gallagher ...................... 604/370 |
| 3,812,001 A | 5/1974 | Ryan ............................. 428/178 |

(Continued)

FOREIGN PATENT DOCUMENTS

| DE | 3512859 | 10/1986 |
| EP | 359391 | 3/1990 |

(Continued)

OTHER PUBLICATIONS

International Search Report and Written Opinion issued in PCT/US2015/065797, dated Mar. 11, 2016.

*Primary Examiner* — Jacqueline F Stephens
(74) *Attorney, Agent, or Firm* — Norton Rose Fulbright US LLP

(57) ABSTRACT

Disposable absorbent articles and methods of making disposable absorbent articles that comprise: an absorbent structure; and a layer of cushion material configured to minimize user perception of hardness or hard spots in the absorbent structure.

27 Claims, 21 Drawing Sheets

(51) Int. Cl.

| | |
|---|---|
| *B32B 37/14* | (2006.01) |
| *B32B 33/00* | (2006.01) |
| *B32B 3/00* | (2006.01) |
| *B32B 5/02* | (2006.01) |
| *B32B 5/08* | (2006.01) |
| *B32B 5/18* | (2006.01) |
| *B32B 7/12* | (2006.01) |
| *B32B 27/06* | (2006.01) |
| *B32B 27/08* | (2006.01) |
| *B32B 27/10* | (2006.01) |
| *B32B 27/12* | (2006.01) |
| *B32B 29/00* | (2006.01) |
| *B32B 29/08* | (2006.01) |
| *B32B 3/04* | (2006.01) |
| *B32B 3/12* | (2006.01) |
| *B32B 3/28* | (2006.01) |
| *B32B 3/30* | (2006.01) |
| *B32B 37/12* | (2006.01) |
| *A61F 13/53* | (2006.01) |

(52) U.S. Cl.
CPC ............... *B32B 5/18* (2013.01); *B32B 7/12* (2013.01); *B32B 27/065* (2013.01); *B32B 27/08* (2013.01); *B32B 27/10* (2013.01); *B32B 27/12* (2013.01); *B32B 29/002* (2013.01); *B32B 29/08* (2013.01); *B32B 33/00* (2013.01); *B32B 37/14* (2013.01); *A61F 2013/15024* (2013.01); *A61F 2013/53081* (2013.01); *A61F 2013/530226* (2013.01); *A61F 2013/530489* (2013.01); *A61F 2013/530649* (2013.01); *B32B 37/12* (2013.01); *B32B 37/1292* (2013.01); *B32B 2262/0253* (2013.01); *B32B 2262/0276* (2013.01); *B32B 2262/062* (2013.01); *B32B 2262/065* (2013.01); *B32B 2262/12* (2013.01); *B32B 2262/14* (2013.01); *B32B 2264/0214* (2013.01); *B32B 2266/025* (2013.01); *B32B 2266/0228* (2013.01); *B32B 2266/0278* (2013.01); *B32B 2266/08* (2013.01); *B32B 2307/718* (2013.01); *B32B 2307/726* (2013.01); *B32B 2307/7265* (2013.01); *B32B 2307/732* (2013.01); *B32B 2309/105* (2013.01); *B32B 2555/02* (2013.01)

(58) Field of Classification Search
CPC .......... B32B 2266/08; B32B 2307/718; B32B 2307/726; B32B 2307/7265; B32B 2307/732
See application file for complete search history.

(56) References Cited

U.S. PATENT DOCUMENTS

| | | | | |
|---|---|---|---|---|
| 4,643,727 | A | | 2/1987 | Rosenbaum .................. 604/369 |
| 4,646,362 | A | * | 3/1987 | Heran ............... A61F 13/49009 2/400 |
| 4,723,953 | A | | 2/1988 | Rosenbaum et al. ......... 604/369 |
| 4,846,821 | A | | 7/1989 | Lyons et al. .................. 604/369 |
| 4,962,769 | A | | 10/1990 | Garcia .......................... 128/889 |
| 5,192,606 | A | | 3/1993 | Proxmire et al. ............. 428/171 |
| 2002/0020142 | A1 | | 2/2002 | Swiszcz et al. ............. 52/783.1 |
| 2003/0069555 | A1 | | 4/2003 | Erdman ....................... 604/369 |
| 2005/0148967 | A1 | | 7/2005 | Baratian et al. ............. 604/367 |
| 2007/0045903 | A1 | | 3/2007 | Day et al. .................... 264/454 |

FOREIGN PATENT DOCUMENTS

| | | |
|---|---|---|
| GB | 2042343 | 9/1980 |
| JP | 57183405 | 11/1982 |

\* cited by examiner

ABSORBENT ARTICLE WITH CUSHION LAYER DEFINING AIR POCKETS

CROSS REFERENCE TO RELATED APPLICATION

This application claims priority to U.S. Provisional Patent Application No. 62/091,929, filed Dec. 15, 2014, which is incorporated by reference in its entirety.

FIELD OF INVENTION

The present invention relates generally to disposable absorbent products such as infant diapers, adult incontinence briefs, pull-up underwear, bladder control pads, bed pads.

BACKGROUND

Absorbent articles, such as baby diapers, training pants, adult incontinence products and other such absorbent products include a topsheet that is closest to the wearer, an outer, moisture-impermeable backsheet, and an absorbent core. Disposable absorbent products have met with widespread acceptance in the marketplace for a variety of applications, including infant and adult incontinence care, in view of the manner in which such products can provide effective and convenient liquid absorption and retention while maintaining the comfort of the wearer. Softness and ability to provide comfort while product is being worn by a wearer is paramount to the acceptance of the product. Perception of the softness by a user or caregiver taking the product out of its packaging is equally important. If a caregiver or user senses the hard spots and superabsorbent polymer (SAP) particles through the outer cover, could lead to negative perception of the product and its efficacy.

Softness of the nonwoven backsheet depends on visual, auditory, and tactile signals. The tactile softness signal is perceived most during use and when the product is first touched by the user. The tactile signal of absorbent articles is mostly perceived via an outer cover that has the nonwoven backsheet and topsheet. The tactile softness signal exhibited by the outer cover depends on the flexibility of nonwoven fibers, pliability, surface friction characteristics, loose fibers or free fiber ends, amount of fibers, and the cushiness of these elements.

Significant efforts have been made to improve the tactile signals when handling absorbent products. Conventional means of improving tactile signals include embossing with soft calender patterns, an increase in basis weight, increase in fiber density to increase loft, alterations in resin chemistry, adding soft additives, slip agents, bi-component fiber technology, hydro entangling, and hydro engorging. These approaches are unfavorable because they drive up raw material costs. Yet another limitation is that soft calendar patterns, bi-component fiber nonwoven, additives, spin finishes, and slip agents all have an adverse effect of decreasing mechanical properties, such as tensile strength, of the absorbent article.

Prior methods of providing a soft back sheet and poly film laminate outercover include the multiple limitations. First, there is a constant desire to run production lines faster in order to reduce manufacturing costs. However, when production line speeds increase, a probability of having uneven regions per unit area in an absorbent core of the product also increases. When these uneven regions are compressed for packaging, hard spots are formed. Hard spots may appear more pronounced in particular when using relatively high production speeds and for relatively thin absorbent cores.

Secondly, there is constant desire to go towards thinner and thinner outercover laminates to achieve desired cost structure. The relatively thin backsheet and poly films allow for hard spots and SAP particles to protrude and poke easily through the poly film/backsheet laminate.

Furthermore, there is a trend towards thinner absorbent products has been driven by a desire for absorbent products to take up less space for transport and storage. Thus, absorbent products are packaged by compressing the absorbent product between compression rolls to reduce its thickness. This increased compression levels can lead to hard spots that protrude and poke through the poly film/backsheet laminate, thereby adversely affecting the softness signal. Another limitation is that a reduction in the compression in package and/or increasing the package size will adversely affect the cost strategy.

Hard-spots can be felt by a user are caregiver of the absorbent product both before use, e.g., taking product out of bags, and in use. Being relatively stiff, the hard-spots may be perceived by a user as causing a less comfortable and less efficient product. These hard spots felt by user could lead to significant negative impact on the overall softness and comfort in case of bed pads and adult incontinent products and can lead to bed sore and rashes.

SUMMARY

This disclose includes embodiments of disposable absorbent articles and methods of making disposable absorbent articles that comprise: an absorbent structure; and a layer of cushion material configured to reduce user perception of hardness or hard spots in the absorbent structure.

Some embodiments of the present disposable absorbent articles comprise: an absorbent structure; a nonwoven fabric; and a layer of cushion material disposed between the nonwoven fabric and the absorbent structure, the layer of cushion material defining a plurality of air pockets; where the layer of cushion material and the nonwoven fabric form a composite having an uncompressed thickness of between 0.4 millimeters and 8.5 millimeters, and a thickness of between 0.1 millimeters and 5.0 millimeters when subjected to a compressive force of 500 grams. In some embodiments, the layer of cushion material is resilient.

Some embodiments of the present articles further comprise: a film; where the film and the layer of cushion material are both disposed between the nonwoven fabric and the absorbent structure, and where the composite includes the film. In some embodiments, the layer of cushion material is configured to minimize a tactile signal of the absorbent structure through the nonwoven fabric.

In some embodiments of the present articles, the composite includes a z-direction deformation in the range of about 0.12 millimeters to 2.5 millimeters under a compressive force in the range of 50 to 500 grams.

In some embodiments of the present articles, the absorbent structure includes a superabsorbent polymeric (SAP) particulate material. In some embodiments, the absorbent structure includes cellulose fiber.

In some embodiments of the present articles, the layer of cushion material includes a poly film defining the plurality of air pockets. In some embodiments, the poly film is at least partially dimpled, pleated, or embossed, and the poly film is configured to exhibit a deformation in the range of 0.15 mm to 0.3 mm under a compression force in the range of 50 grams to 500 grams. In some embodiments, the layer of cushion material includes a plurality of embossed poly films defining the plurality of air pockets, the plurality of embossed poly films being laminated to each other adhesively, thermally, by co-extrusion, ultrasonically, or any combination thereof.

Some embodiments of the present articles further comprise: a spray or signature in an adhesive pattern with at least one spacing of 10 mm or larger such that the composite is configured to exhibit a deformation in the range of 0.3 mm or more under a compressive force in the range of 50 grams to 500 grams.

In some embodiments of the present articles, the layer of cushion material includes a spunlace nonwoven defining the plurality of air pockets such that the composite is configured to exhibit a deformation in the range of 0.18 mm to 1.2 mm under a compressive force in the range of 50 grams to 500 grams. In some embodiments, the spunlace nonwoven include fibers with 60% or more of a PET fiber blend.

In some embodiments of the present articles, the layer of cushion material includes a spunlace nonwoven having an embossed pattern facing away from the absorbent structure to define the plurality of air pockets.

In some embodiments of the present articles, the layer of cushion material includes a carded through-air bonded (TAB) nonwoven defining the plurality of air pockets and covering at least the absorbent structure, such that the composite is configured to exhibit a deformation in the range of 0.4 mm or more under a compressive force in the range of 50 grams to 500 grams. In some embodiments, a basis weight of the carded TAB nonwoven is 22 gsm or higher with a fiber composition including any combination of the following: polyester, PP, bi-component fibers of PP-PE, PET-PE, PET/co-PET, PP-PET, cotton, bleached cotton, unbleached cotton, jute, ramie, and flax.

In some embodiments of the present articles, the layer of cushion material includes at least one material selected from the group consisting of: closed-cell polymeric foam, open-cell polymeric foam, bubble wrap, and embossed paper. In some embodiments, at least some of the plurality of air pockets include a shape selected from the group consisting of: honeycomb, square, circular, or randomly varied.

Some embodiments of the present methods (e.g., of assembling an absorbent article) comprise: joining a layer of cushion material and a nonwoven fabric to form a cushion structure, the layer of cushion material including a plurality of air pockets; and positioning the cushion structure on an absorbent structure; where the cushion structure has an uncompressed thickness of between 0.4 millimeters and 8.5 millimeters, and a thickness of between 0.1 millimeters and 5.0 millimeters when subjected to a compressive force of 500 grams.

Some embodiments of the present methods further comprise: joining a bonding fabric to an outwardly facing surface of the cushion structure.

In some embodiments of the present methods, the layer of cushion material is configured to minimize a tactile signal of the absorbent structure on a side of the layer of cushion material opposite the absorbent structure.

In some embodiments of the present methods, the absorbent structure includes a superabsorbent polymeric (SAP) particulate material.

In some embodiments of the present methods, joining the layer of cushion material and the nonwoven fabric includes at least one joining process selected from the group consisting of: thermal bonding, ultrasonic bonding, adhesive lamination, pressure lamination, and co-extrusion.

In some embodiments of the present methods, the layer of cushion material includes at least one material selected from the group consisting of: closed-cell polymeric foam, open-cell polymeric foam, bubble wrap, and embossed paper.

In some embodiments of the present methods, the layer of cushion material includes a carded and through-air bonded nonwoven layer with a basis weight of 20 gsm or higher. Some embodiments further comprise: bonding a liquid-impervious polymeric film to the cushion structure when the cushion structure includes at least one of the open-cell polymeric foam and the embossed paper.

In some embodiments of the present methods, positioning the layer of cushion material includes completely covering the absorbent article with the layer of cushion material.

Some embodiments of the present disposable articles comprise: an absorbent structure; and a layer of cushion material coupled to the absorbent structure such that the layer of cushion material defines a backsheet of the absorbent article, the layer of cushion material defining a plurality of air pockets; where the layer of cushion material has an uncompressed thickness of between 0.4 millimeters and 8.5 millimeters, and a thickness of between 0.1 millimeters and 5.0 millimeters when subjected to a compressive force of 500 grams; and where the layer of cushion material includes at least one material selected from the group consisting of: closed-cell polymeric foam, open-cell polymeric foam, bubble wrap, and embossed paper.

"Hard spots," with respect to absorbent hygiene products, are described as local regions in a core being more compact and stiffer than an overall core.

"Superabsorbent" or "superabsorbent material" or "SAP" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The SAP materials can be natural, synthetic and modified natural polymers and materials. In addition, the SAP materials can be inorganic materials, such as silica gels, or organic compounds such as cross-linked polymers.

"Disposable" refers to articles which are designed to be discarded after a limited use rather than being laundered or otherwise restored for reuse.

"Absorbent core" means a structure typically disposed between a topsheet and backsheet of an absorbent article and containing materials which absorb in absorbent article. The absorbent core may also include a cover layer or envelope material. The cover layer or envelope may comprise; nonwovens, SAP, cellulosic or non-cellulosic materials, films, fibers or substrate made of any one two or all of these combination materials.

"Layer" when used in the singular can have the dual meaning of a single element or a plurality of elements.

"Nonwoven" fabrics, according to an INDA definition, are broadly defined as sheet or web structures bonded together by entangling fiber or filaments (and by perforating films) mechanically, thermally, or chemically. They are flat, porous sheets that are made directly from separate fibers or from molten plastic or plastic film. They are not made by weaving or knitting and do not require converting the fibers to yarn. The basis weight of nonwoven fabrics is usually expressed as gsm or grams per square meter.

"Nonwoven backsheet" is a backing substrate layer in the outer cover. The nonwoven backsheet is most often a nonwoven layer facing away from the wearer. "Film" means a membrane-like layer of material formed of one or more polymers, which does not have a form consisting predominately of a web-like structure of fibers and/or other fibers. Film referred to in this disclosure as "poly film" is a film that is disposed in the outer cover laminate. The poly film can be breathable film or non-breathable.

The term "breathable film," "breathable laminate" or "breathable outer cover material" refers to a film, laminate, or outer cover material having a water vapor transmission rate ("WVTR") of at least about 300 grams/m224 hours. Breathable materials typically rely on molecular diffusion of vapor, and are substantially liquid impermeable.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact.

"Bubble wrap" is a pliable transparent plastic material commonly used for packing fragile items. Regularly spaced, protruding air-filled hemispheres (bubbles) provide cushioning for fragile items.

"Foam material" refers to a material made with the aid of a foaming process. The term "open cell foam material" refers to a foam layer whose cells interconnect, or otherwise create voids from one surface of the layer to the opposite surface. The term "closed cell foam material" refers to a foam layer whose cells are not substantially interconnected.

"Lamination" is the technique of manufacturing a material in multiple layers, so that the composite material has benefits of all the encompassing layers; improved strength, stability, sound insulation, appearance or other properties. A laminate is a permanently assembled object by heat, pressure, welding, or adhesives.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Deformation," with regard to the substrates mentioned herein, refers to the percent change in length that occurs while the material is stressed or compressed.

"Machine direction" (MD), with respect to the making of a nonwoven web material, refers to the direction along the material or laminate substantially parallel to the direction of forward travel of the material or laminate through the manufacturing line in which the material or laminate is manufactured. "Cross direction" (CD), with respect to the making of a nonwoven or laminate, refers to the direction along the material substantially perpendicular to the direction of forward travel of the material through the manufacturing line in which the material and/or article is manufactured. "Z-direction," means perpendicular to plane approximated by the web along machine and cross direction.

"Asymmetric embossed" is an embossed paper towel in which each layer of the papers has its own embossing pattern such that when the layers of paper are combined together by bonding, they have significant lofty and cushiness due to asymmetry and embossing.

"Aero-soft materials" refers to the soft materials that have ability to incorporate or entrap or hold on to air and exhibits cushiness or softness.

The term "coupled" is defined as connected, although not necessarily directly, and not necessarily mechanically. The terms "a" and "an" are defined as one or more unless this disclosure explicitly requires otherwise.

Further, a device or system that is configured in a certain way is configured in at least that way, but it can also be configured in other ways than those specifically described.

The terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, an apparatus that "comprises," "has," "includes," or "contains" one or more elements possesses those one or more elements, but is not limited to possessing only those elements. Likewise, a method that "comprises," "has," "includes," or "contains" one or more steps possesses those one or more steps, but is not limited to possessing only those one or more steps.

Any embodiment of any of the apparatuses, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Some details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. Views in the figures are drawn to scale (unless otherwise noted), meaning the sizes of the depicted elements are accurate relative to each other for at least the embodiment in the view.

DETAILED DESCRIPTION OF ILLUSTRATIVE EMBODIMENTS

Figure 1:
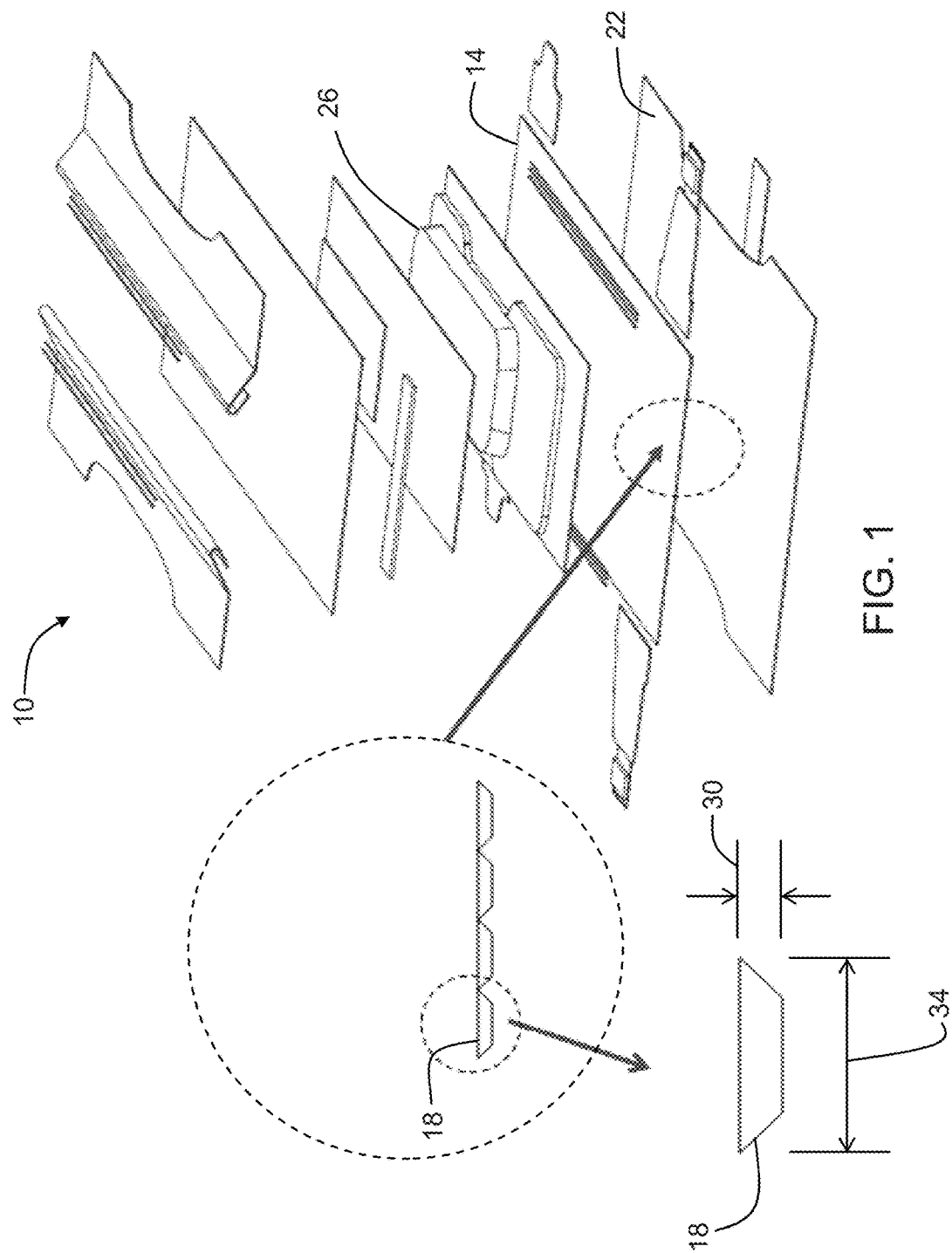
FIG. 1 depicts an absorbent article having a poly film that includes a plurality of air pockets.

Referring now to the drawings, and more particularly to FIG. 1, shown therein is an example of an absorbent article 10 having a poly film 14 that includes a plurality of air pockets 18. For example, the poly film 14 may include microscopic air bubbles. In this embodiment, absorbent article 10 is configured as a diaper; in other embodiments, the present absorbent articles can be configured as pads and/or the like. Absorbent article 10 includes poly film 14, a backsheet 22, such as a nonwoven, and an absorbent structure 26. In some embodiments, absorbent structure 26 includes cellulose fibers and/or superabsorbent polymeric (SAP) particulate material. Air pockets 18 are configured such that absorbent structure 26 is not be felt by a user handling absorbent article 10.

In some embodiments, air pockets 18 are configured to protrude in a z-direction out of a general plane of backsheet 22 and away from a wearer. In this configuration, air pockets 18 are configured to face away from the wearer such that the dips and hills between air pockets 18 can be felt through backsheet 22 by the user handling absorbent article 10. For example, air pockets 18 create a layer of springy loft which enhances a softness felt by the user handling absorbent article 10. By blocking irritating signals caused by hard spot and/or SAP protrusions, the user feels a tactile soft cushiness signal when the absorbent article 10 is in use or when the absorbent article 10 is being removed from packaging.

Air pocket height 30 and length 34 can be selected such that air pockets 18 will not hinder compression of absorbent article 10 during processing or packaging. For example, air pocket height 30 and length 34 are selected such that poly film 14 withstands packaging compression and that when the user takes absorbent article 10 out of its packaging, between 70% and 95% such as 80% of air pocket height 30, softness, and/or cushioning effect is regained.

Figure 2B:
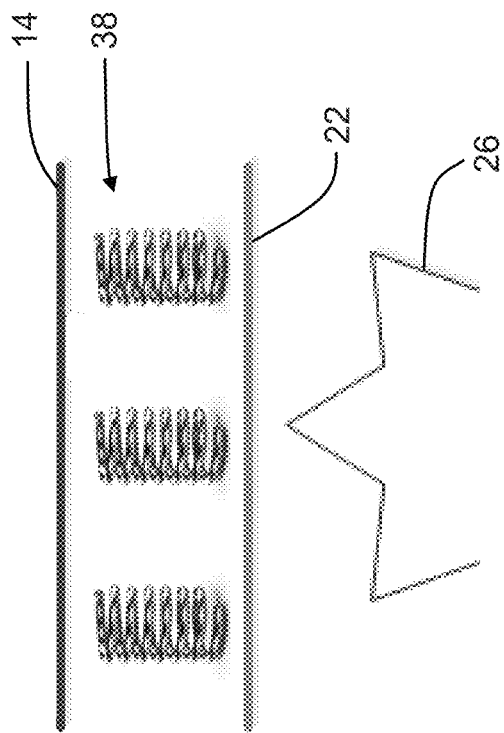
FIGS. 2A-2B depict schematic views of a concept of having a layer of cushion material disposed in an outer cover.
Figure 2A:
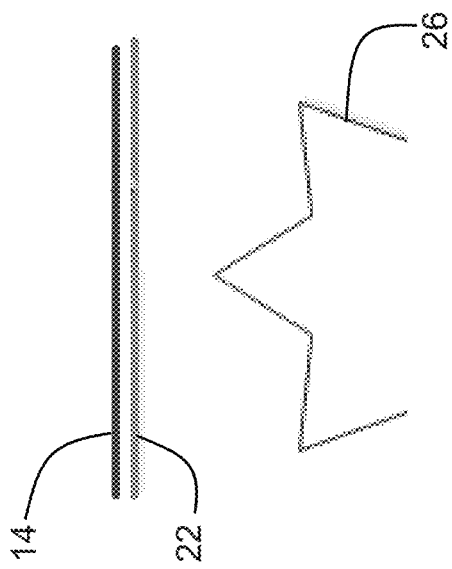

FIG. 2A shows a schematic of a poly film 14/backsheet 22 laminated outer cover. In some embodiments, z-direction deformation is built in between poly film 14 and backsheet 22. For example, a layer of cushion material 38 is disposed between poly film 14 and backsheet 22 (shown schematically in FIG. 2B). Alternatively, layer of cushion material 38 is disposed between backsheet 22 and absorbent structure 26. In other embodiments, z-direction deformation is built within poly film 14. For example, layer of cushion material 38 and poly film 14 are integrally formed.

Layer of cushion material 38 may include any appropriate material configured to have a higher compressibility than absorbent structure 26. Layer of cushion material 38 includes the plurality of air pockets 18. Air pockets 18 are configured to increase comfort, and reduce bed sores and rashes for the user.

In some embodiments, air pockets 18 are formed on a flat surface, such as a film. In some embodiments, air pockets 18 are laminated between two films. Air pockets 18 may be coupled end to end. Air pockets 18 may be configured such that they face away from the wearer of absorbent article 10. For example, air pockets 18 are disposed on an outer side of absorbent article 10, away from the wearer.

Figure 3A:
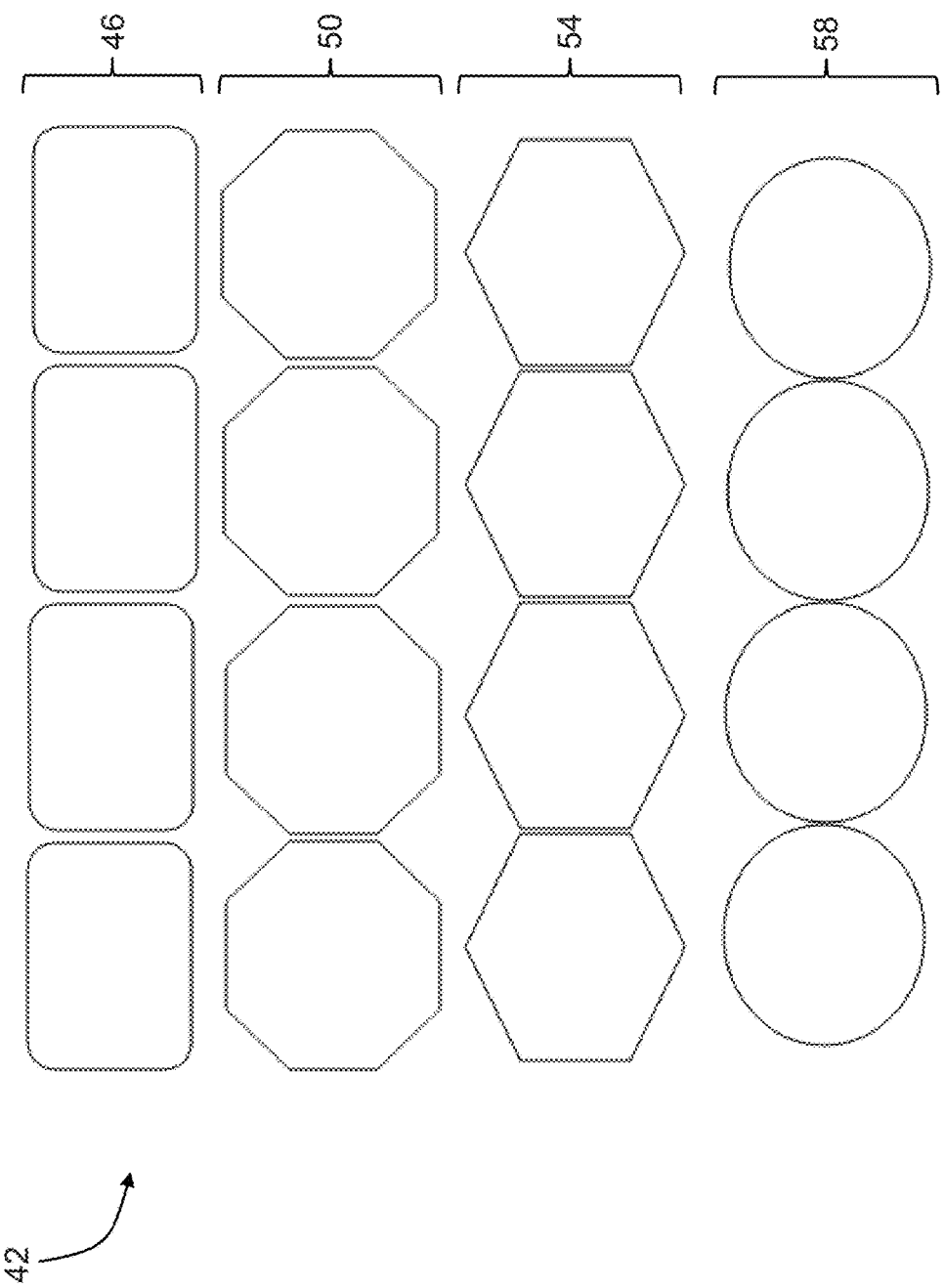
FIG. 3A depicts a top view of a plurality of air pocket configurations.
Figure 3B:
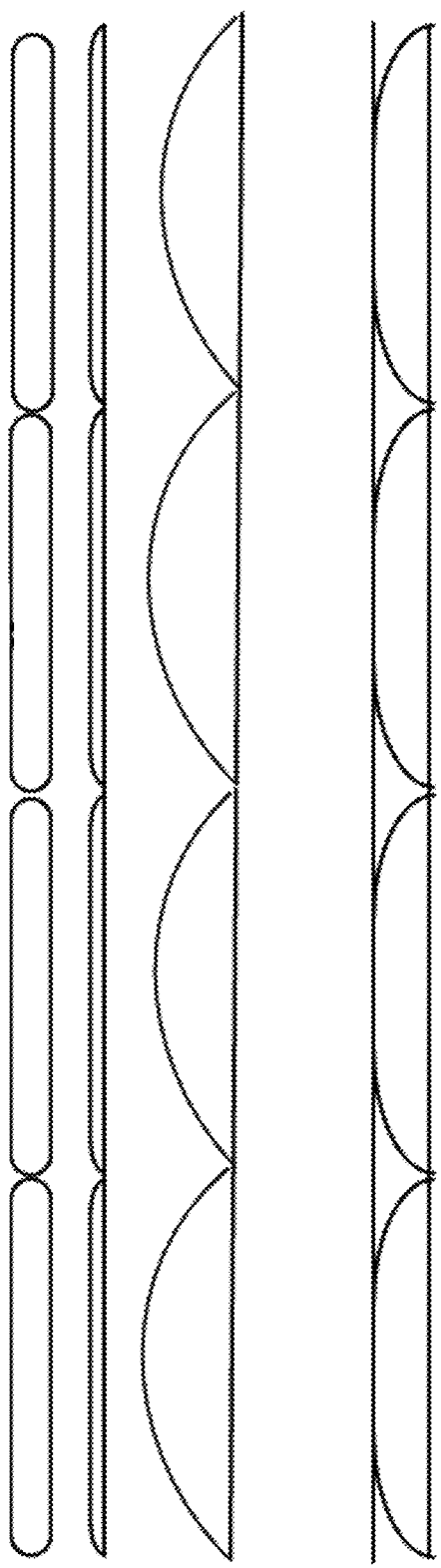
FIG. 3B depicts a cross section view of a plurality of air pocket configurations.

FIG. 3A shows a top view of a plurality of air pocket configurations 42 and FIG. 3B shows a cross section view of a plurality of air pocket configurations. The air pocket designs include any appropriate shape, such as square 46, octagonal 50, honeycomb 54, circular 58 or any combination thereof. Air pockets 18 may be arranged randomly or in any suitable pattern corresponding to the shape of air pockets 18. The air pocket design may be selected based on a three-dimensional profile which provides a maximum softness, drape, and processing benefits. In one example, the pattern formed by the air pockets provides a three-dimensional backsheet appearance visible to the user.

Figure 4:
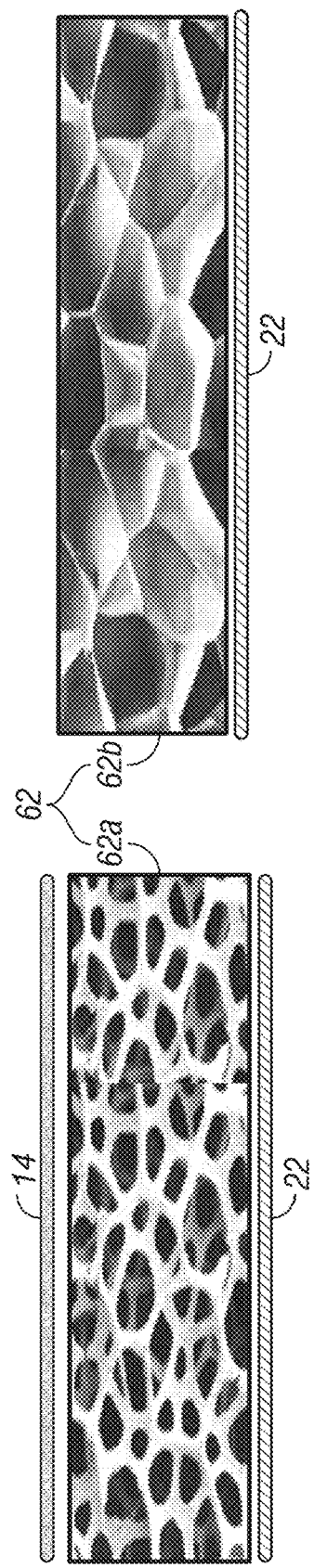
FIG. 4 depicts schematic cross-section views of a laminate having foam film open-cell and foam film closed-cell structures.

In other embodiments, layer of cushion material 38 includes a foam film 62. Foam film 62 may include open-cell structures 62a or closed-cell structures 62b, as shown in FIG. 4, or a combination thereof. Layer of cushion material 38 having closed-cell foam film 62b may or may not include poly film 14 thereon. Layer of cushion material 38 having open-cell foam film 62a includes poly film 14 on an outward-facing surface thereof. Closed-cell 62b and open-cell 62a foam films are commercially available and supplied by companies such as Polyair, FXI, Woodbridge Foam Fabricating, and IVEX Specialty Paper. Polyurethane, polyethylene (PE) foam blocks, PE, polypropylene and polystyrene resins may be used to make foam films 62.

Figure 5:
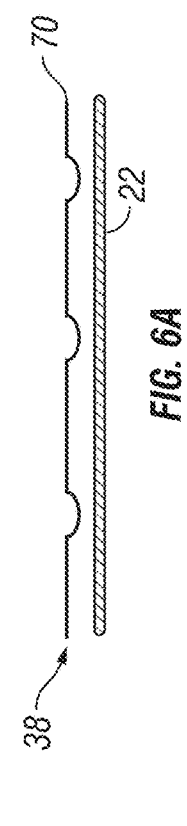
FIG. 5 depicts a laminate having an asymmetric embossed paper.

FIG. 5 shows an embodiment of layer of cushion material 38 having one or more embossed papers 66, such as a paper towel or soft toilet tissue. For example, paper 66 includes an embossed pattern and a significant z-direction thickness and/or three-dimensional cross section. As shown in FIG. 5, paper 66 is disposed between poly film 14 and backsheet 22. The embossing on paper 66 may be symmetrical or asymmetrical, as shown. For example, the embossing in each paper 66 may be aligned or misaligned with the embossing in a successive paper 66. In some embodiments, poly film 14 is disposed on an outward-facing surface of embossed paper 66. Embossed paper towels are commercially available and sold under brands such as Bounty and Scotts.

Figure 6A:
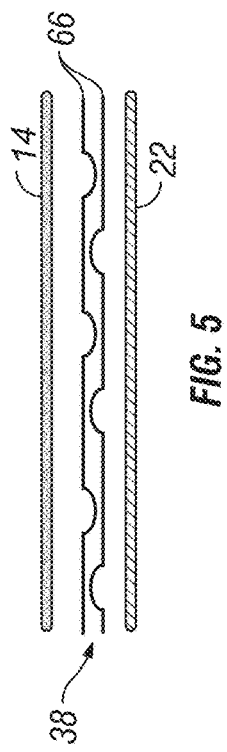
FIG. 6A depicts a laminate having an embossed or pleated poly film and a backsheet.
Figure 6C:
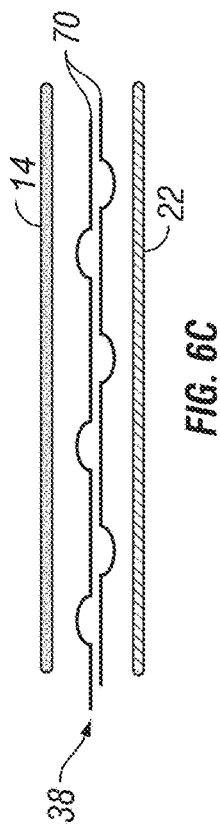
FIG. 6C depicts a laminate having a poly film, a backsheet, and two laminated poly films therebetween.
Figure 6B:
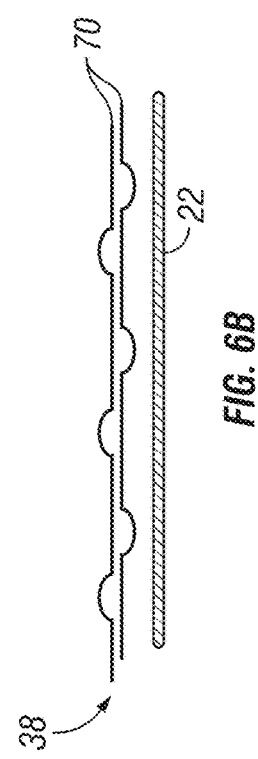
FIG. 6B depicts a laminate having two embossed poly films and a backsheet.

In other embodiments, layer of cushion material 38 includes a poly film 70 having embossing thereon such that when poly film 70 is laminated to backsheet 22, poly film 70 and backsheet 22 form air pockets 18 therebetween. As shown, the poly film 70 may be directly laminated to the backsheet 22, as shown in FIG. 6A. Alternatively, a plurality of poly films 70 may be joined to form a plurality of air pockets 18 therebetween, as shown in FIGS. 6A and 6B. The plurality of poly films 70 may be joined together thermally, adhesively, and/or ultrasonically to form the air pockets 18. Poly film 70 laminated to backsheet 22 may or may not include poly film 14 thereon.

Figure 7A:
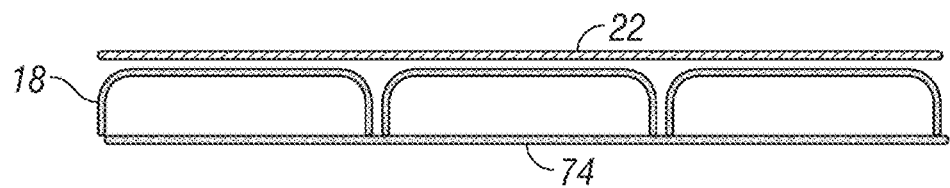
FIGS. 7A-7B depict schematics of air pockets in bubble wrap.
Figure 7B:
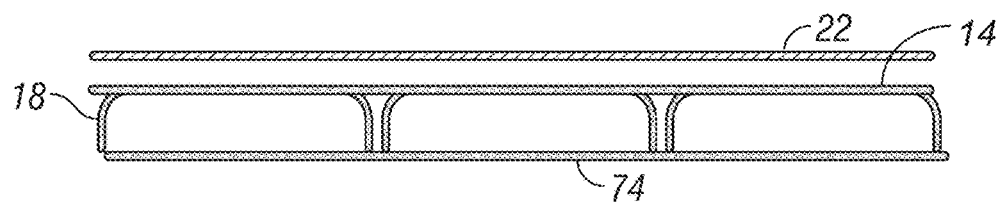

In some embodiments, layer of cushion material 38 includes bubble wrap 74 having air pockets 18. In one example, bubble wrap 74 is laminated with poly film 14 and joined with backsheet 22, as shown in FIG. 7B. In another example, air pockets 18 in bubble wrap 74 are enclosed by backsheet 22, as shown in FIG. 7A. Alternatively, air pockets 18 in bubble wrap 74 are exposed to the user. Bubble wrap 74 is commercially available and supplied by companies such as Nefab Packaging, Polyair, and Sealed Air.

In other embodiments, layer of cushion material 38 includes a polyfilm with micro pleats.

In other embodiments, layer of cushion material 38 includes spunlace nonwovens and spunlace nonwoven laminates between poly film 14 and backsheet 22. For example, the spunlace nonwovens may include a PET fiber blend, which may be commercially obtained from Spuntech, Jacob Holmes, PGI Nonwovens, or Fitesa.

In other embodiments, layer of cushion material 38 includes carded and through air bonded nonwovens. Such carded and through air bonded nonwoven can be commercially obtained from companies such as Texsus, Shalag, Freudenberg, PGI Nonwovens, Fitesa, or Berry Plastics.

Figure 8:
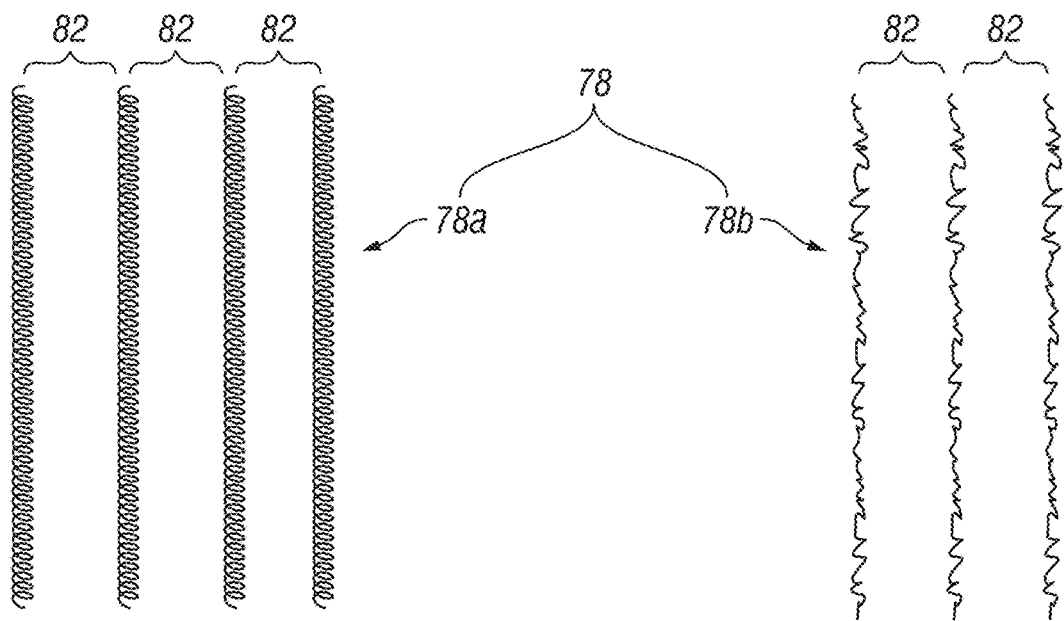
FIG. 8 depicts adhesive patterns in a laminate.

Lamination may be provided using adhesive lamination (ADH). Third party laminators, such as Web Industries and Tufco, may also provide lamination services suitable to join layer of cushion material 38, poly film 14, and/or backsheet 22. In some embodiments, adhesive patterns 78 used in lamination may form a plurality of air pockets 18 between poly film 14 and absorbent structure 26. For example, air pockets 18 may be formed by varying a distance 82 between a spray 78*a* or signature 78*b* adhesive pattern used to laminate poly film 14 and backsheet 22. Distances 82 in adhesive patterns 78 are shown in FIG. 8.

In some embodiments, poly film 14 having the plurality of air pockets 18 is joined to backsheet 22 by thermal bonding, co-extrusion lamination and/or adhesive lamination. As a result, a volume between air pockets 18 may not be bonded to backsheet 22. The volume between air pockets 18 will not restrict backsheet 22. The volume serves as a hinge point and provides additional drape to poly film 14/backsheet 22 laminate. In some embodiments, the volume between air pockets 18 appears loftier and, as a result, air pockets 18 appear more pronounced and visually clearly defined to the user.

Figure 9A:
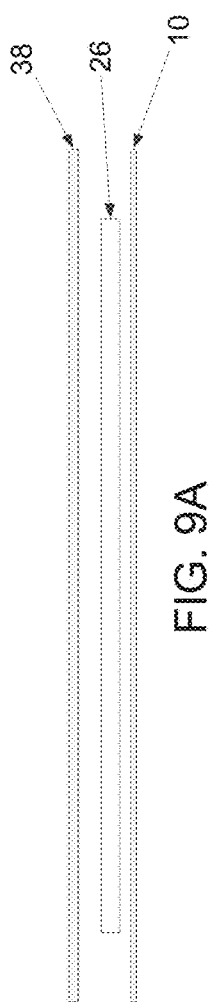
FIGS. 9A-C and 10 depict a coverage area of a layer of cushion material on the absorbent article.
Figure 9B:
Figure 9C:
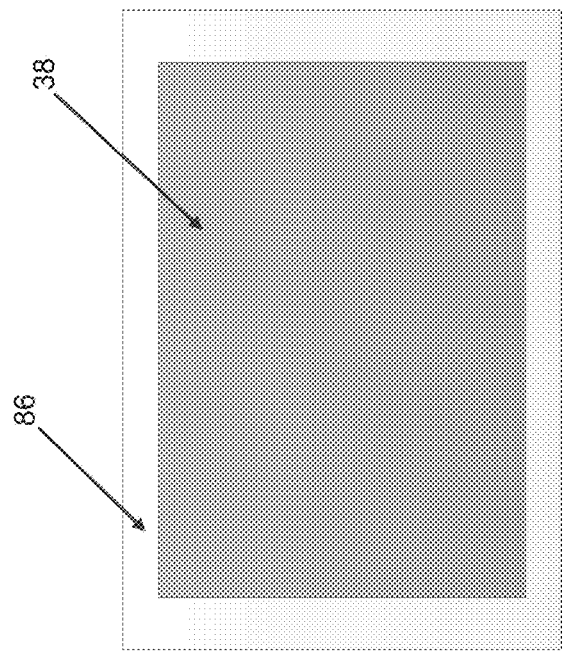
Figure 10:
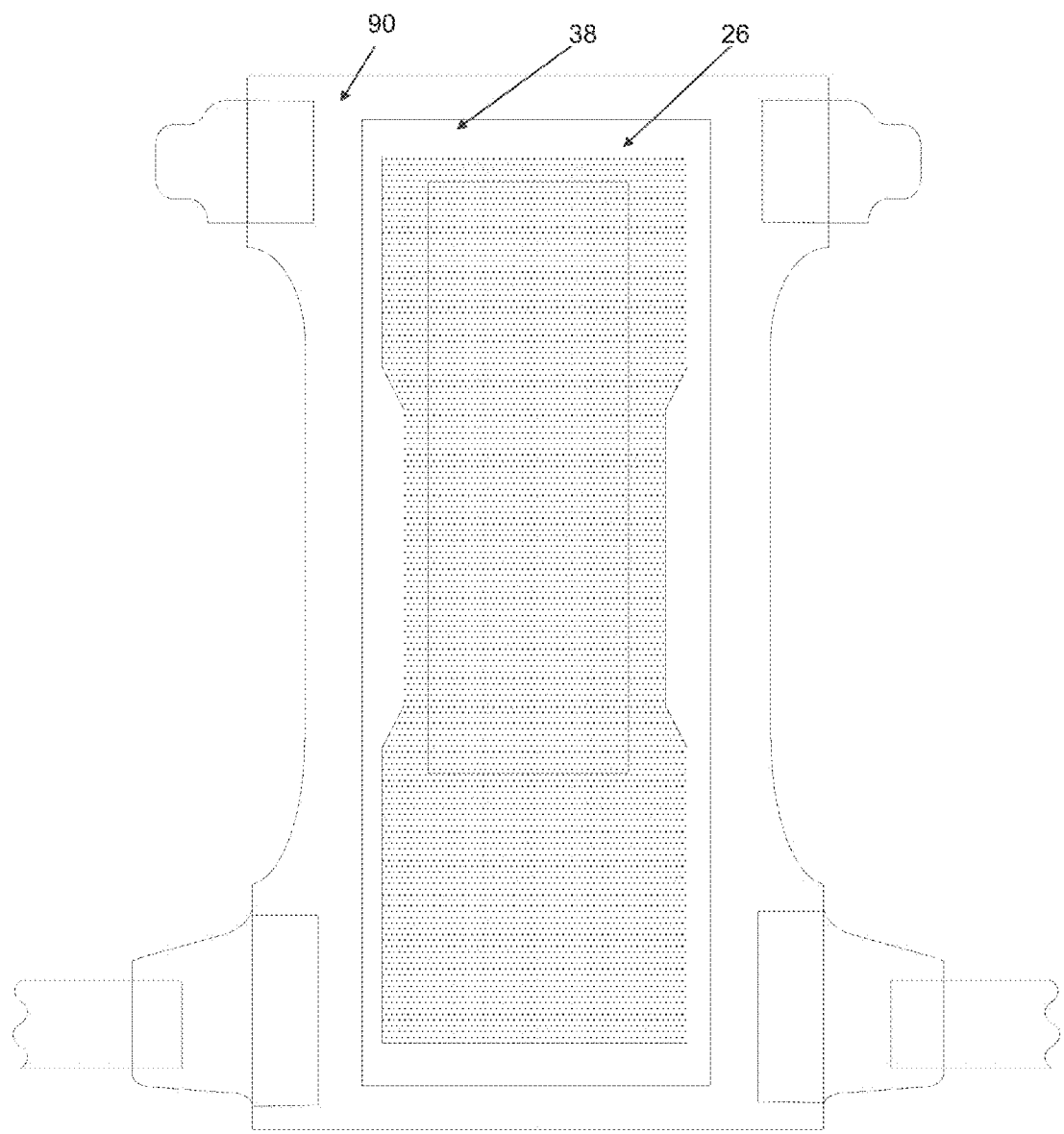

In some embodiments, layer of cushion material 38 covers an entire width of absorbent article 10 as shown in FIG. 9A. Alternatively, layer of cushion material 38 covers an area of absorbent article 10 where absorbent structure 26 is located, as shown in FIG. 9B. In one example, layer of cushion material 38 covers a portion of a bed pad 86 only where absorbent structure 26 is located, as shown in FIG. 9C. In another example, layer of cushion material 38 covers a portion of a diaper 90 where absorbent structure 26 is located, as shown in FIG. 10.

EXAMPLES AND TEST DATA

Figure 11:
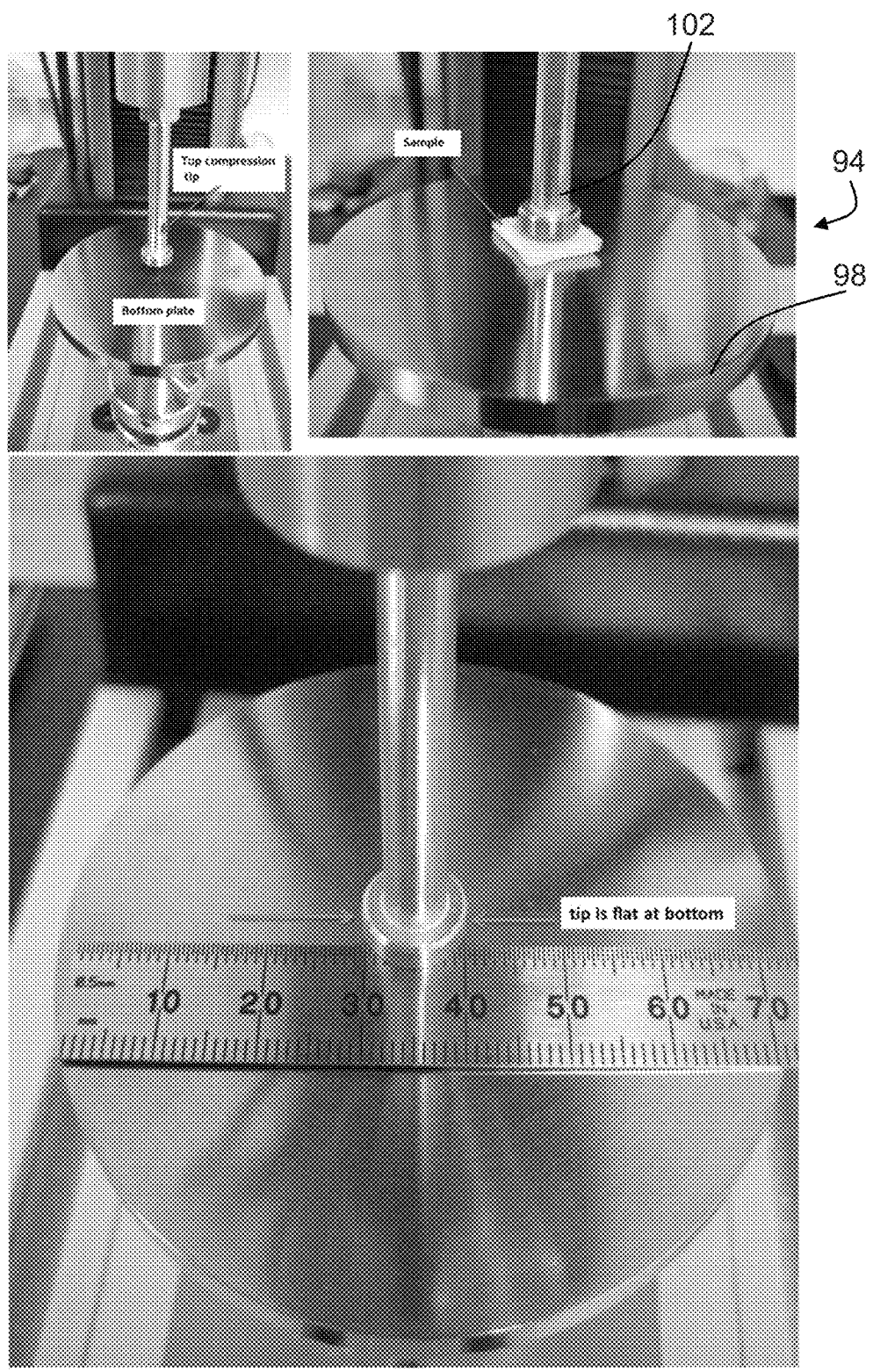
FIG. 11 depicts a compression apparatus used to test laminates having the layer of cushion material.

A compression test may determine the cushion or tactile cushion softness exhibited by a sample laminate of each embodiment described herein. FIG. 11 shows a representative example of a compression test apparatus 94. Apparatus 94 includes a stationary flat plate 98 and a flat-faced compression rod 102 driven downward towards flat plate 98 by a motor. A height mode may be used to measure a thickness of the sample laminate. For the compression test, each sample laminate has a predetermined volume, such as 4 cm$^2$. The sample laminate may be placed between flat plate 98 and compression rod 102. The sample laminate may be compressed at a constant rate up to a maximum preset load. The sample laminate may be preloaded by touching rod 102 with a top surface of the sample laminate. The sample laminate may be compressed at 5 mm/min to a load of 500 gram force. An initial thickness of the sample laminate before loading is measured. Then, a final thickness of the sample laminate at 500 grams is measured. The compression test described herein was used to obtain the following data.

The table below displays measurements of a pre-load height of the sample material (HT-PL) and a height under an applied compression load of 500 grams (HT-LD). When a caregiver or user of absorbent article perceives the tactile cushiness of laminate sample they typically use the end of an index finger, hyponychium, and apply a force in the range of 50 grams to maximum of 500 grams. The present testing therefore examined extension and height change in samples for force in the range of 50 grams to 500 grams.

| Sample | Material description | HT-PL (mm) | HT-LD (mm) |
| --- | --- | --- | --- |
| DPC poly | 0.6 mil polypropylene poly | 0.06 | 0.04 |
| Lamifoam film 1/32 | Lamifoam film 1/32" thick by POLYAIR | 0.75 | 0.38 |
| Lamifoam film 1/16 | Lamifoam film 1/16" thick by POLYAIR | 1.39 | 0.85 |
| Cruisers poly film only | Poly film from commercially available Cruisers product | 0.05 | 0.03 |
| FXI foam on poly | 0.06" thick FXI polyurethane foam film on 0.6 mil polypropylene poly | 1.55 | 0.24 |
| Swadlers poly | Swadlers poly | 0.03 | 0.03 |
| DPC poly-backsheet | 13.5 gsm pgi nonwoven and 0.6 mil polypropylene poly | 0.26 | 0.11 |
| FXI foam-poly-nonwoven laminate | FXI foam between 0.6 mil polypropylene poly-13.5 gsm pgi nonwoven laminate | 1.69 | 0.37 |
| Huggies platinum backsheet-poly laminate | commercially available Huggies platinum product backsheet-poly laminate | 0.37 | 0.11 |
| STARFOAM 1/32-NW Laminate | STARFOAM 1/32"-13.5 gsm pgi nonwoven Laminate | 0.99 | 0.53 |
| STARFOAM 1/16-NW Laminate | STARFOAM 1/16"-13.5 gsm SMS nonwoven Laminate | 1.65 | 0.73 |
| Cruisers backsheet-poly laminate | commercially available cruisers product backsheet-poly laminate | 0.37 | 0.13 |
| Lamifoam film 1/32-nonwoven laminate | Lamifoam film 1/32"-13.5 gsm pgi nonwoven laminate | 0.94 | 0.53 |
| Lamifoam film 1/16-nonwoven laminate | Lamifoam film 1/16"-13.5 gsm pgi nonwoven laminate | 1.53 | 0.92 |
| Huggies platinum backsheet-poly laminate | commercially available Huggies platinum backsheet-poly laminate | 0.37 | 0.11 |
| LAMI-BUBWRAP-nonwoven laminate | 4 mm thick Lami-Bubble wrap film-13.5 gsm pgi nonwoven laminate | 4.01 | 1.67 |
| BUBLEWRAP-NWL | 2.9 mm Bubble wrap material-13.5 gsm pgi nonwoven laminate | 2.9 | 0.65 |

-continued

| Sample | Material description | HT-PL (mm) | HT-LD (mm) |
| --- | --- | --- | --- |
| Paper towel on poly | Paper towel on 0.6 mil polypropylene poly | 0.94 | 0.39 |
| soft toilet tissue | commercially available soft toilet tissue | 0.53 | 0.26 |
| nonwoven-soft toilet tissue-poly | 13.5 gsm pgi nonwoven-soft toilet tissue-0.6 mil polypropylene poly laminate | 0.73 | 0.36 |
| Paper towel between nonwoven and poly | Paper towel between 13.5 gsm pgi nonwoven and 0.6 mil polypropylene poly | 0.93 | 0.54 |

Figure 12:
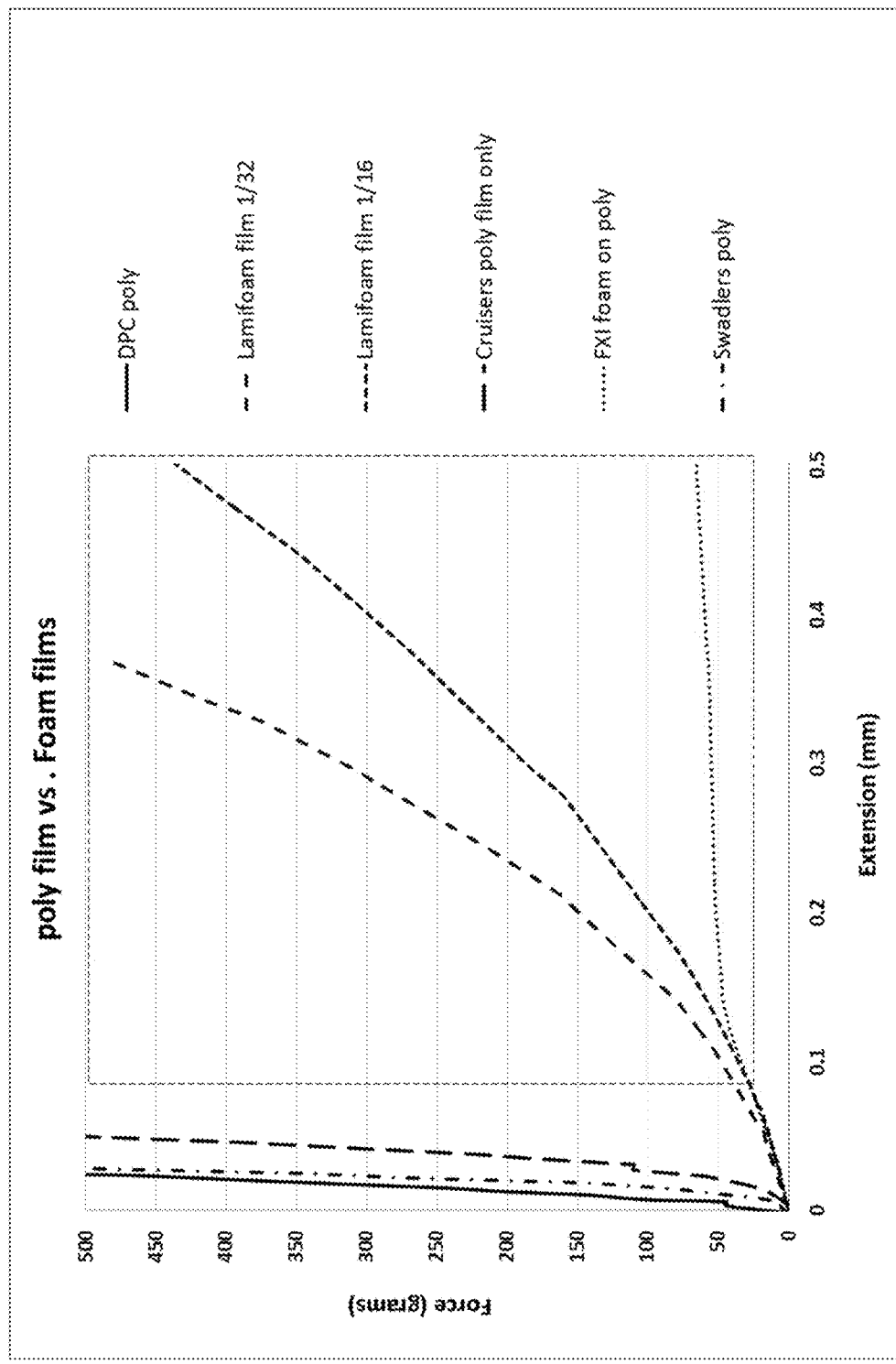
FIGS. 12-21 depict compression force versus deformation test data measured by the compression apparatus for various laminates having the layer of cushion material.

FIG. 12 shows a compression versus extension plot comparing existing Domtar Personal Care ("DPC") poly film and various foam films. DPC poly film is 0.6 mil thick polypropylene film that can be commercially sourced from manufacturers such as Berry Plastics Corporation and Clopay Plastic Products. Two types of bubble wrap materials were tested: a bubble wrap which had thickness of 2.9 millimeters and a lami-bubble wrap material which had thickness of 4 millimeters. Lami-bubble wrap is a bubble wrap with additional film laminated on a top surface, as shown in FIG. 7B.

As shown in the table above, foam films both 1/32" and 1/16" thick exhibited more cushioning than the DPC poly film and other poly films that are found in commercially available diaper products in market. DPC poly film undergoes a thickness change of 0.02 millimeters, which is negligible when compared to a thickness change exhibited by an aero-soft laminate, e.g., Lamifoam film 1/32-nonwoven laminate, which exhibited a thickness change of approximately 0.4 millimeters. Under a force of 50 grams to 500 grams, the DPC poly film and poly film found in commercially available absorbent products in market place exhibited a deformation of 0.1 millimeters or less, whereas, the foam film or soft materials have 0.1 millimeters or greater deformation or extension along an x-axis. Compression test data showed that laminate exhibited cushiness when it experienced more deformation along the x-axis, as shown by the dotted line box in FIG. 12. When the laminate includes aero-soft materials or materials which include air cushion materials, such as those shown in FIG. 2B, the laminate exhibits more z-directional deformation or more elongation or deformation on x-axis. Testing was also performed on poly film/nonwoven backsheet laminates currently commercially available, DPC poly film-backsheet laminate, and soft material laminates. DPC poly-backsheet laminate is an outer cover laminate found in DPC diapers. The DPC poly film/backsheet laminate includes 13.5 gsm PGI nonwoven and 0.6 mil polypropylene poly film. Open cell foam-poly film laminate included a 0.06 inch thick open cell polyurethane foam film, which can be obtained from FXI, laminated to a 0.6 mil polypropylene poly film.

Figure 13:
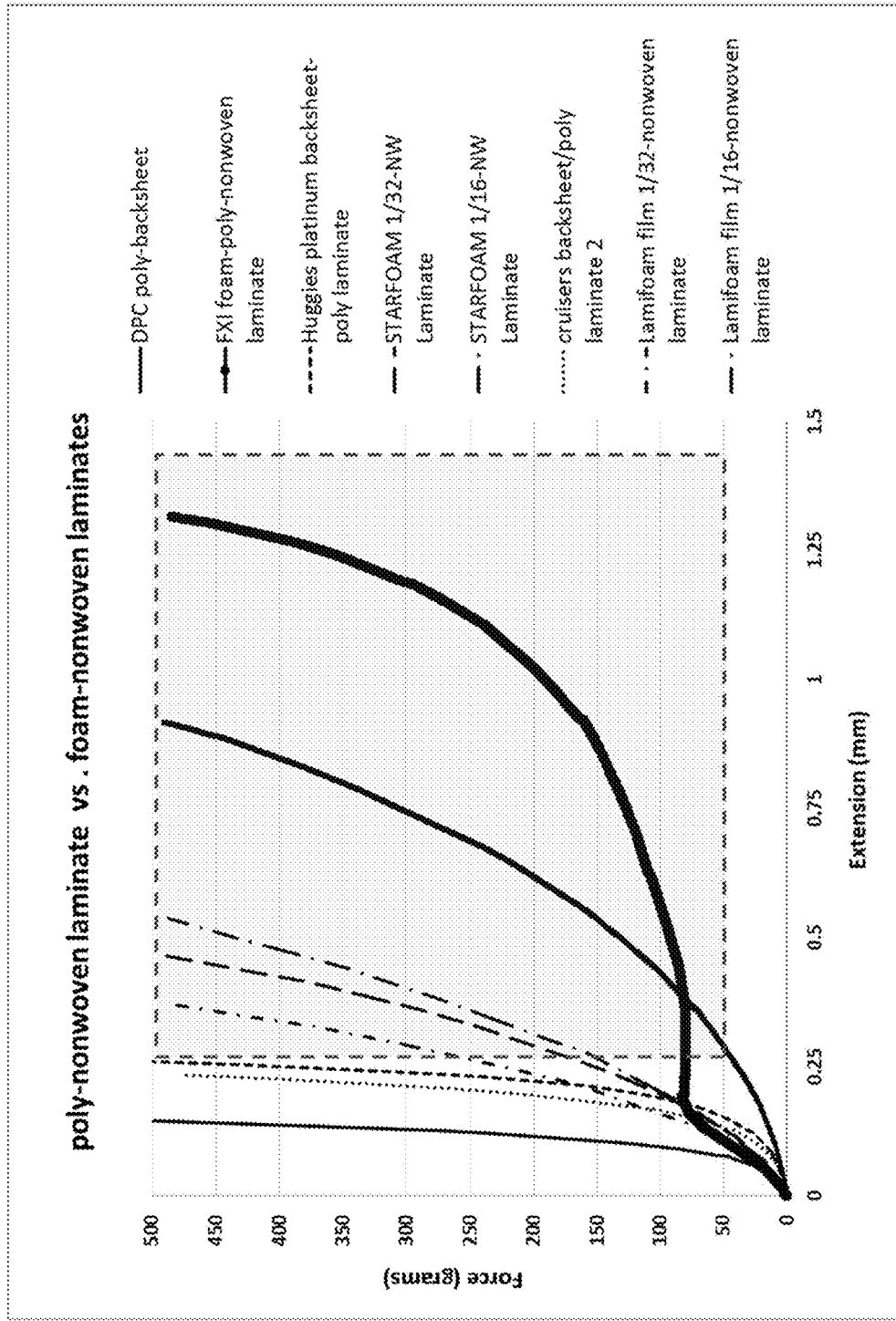

FIG. 13 shows a compression versus extension plot comparing DPC poly film/backsheet laminate, competitors' outer cover laminates, and foam film/backsheet laminates. Compared to DPC poly film/backsheet laminate and competitors' products (cruisers outer cover, Haggies platinum outer cover), foam film/backsheet laminates exhibited significant tactile softness signals. The FXI foam-poly-nonwoven sample, which included the 0.06 inch thick open-cell foam film laminated between 13.5 gsm PGI nonwoven and 0.6 mil polypropylene poly film, exhibited double peak-deformation and peak zones. Results showed that foam film/backsheet laminates exhibited a deformation range of 0.25 mm to 1.25 mm under a compression range of 50 grams to 500 grams using the compression test described herein.

Figure 14:
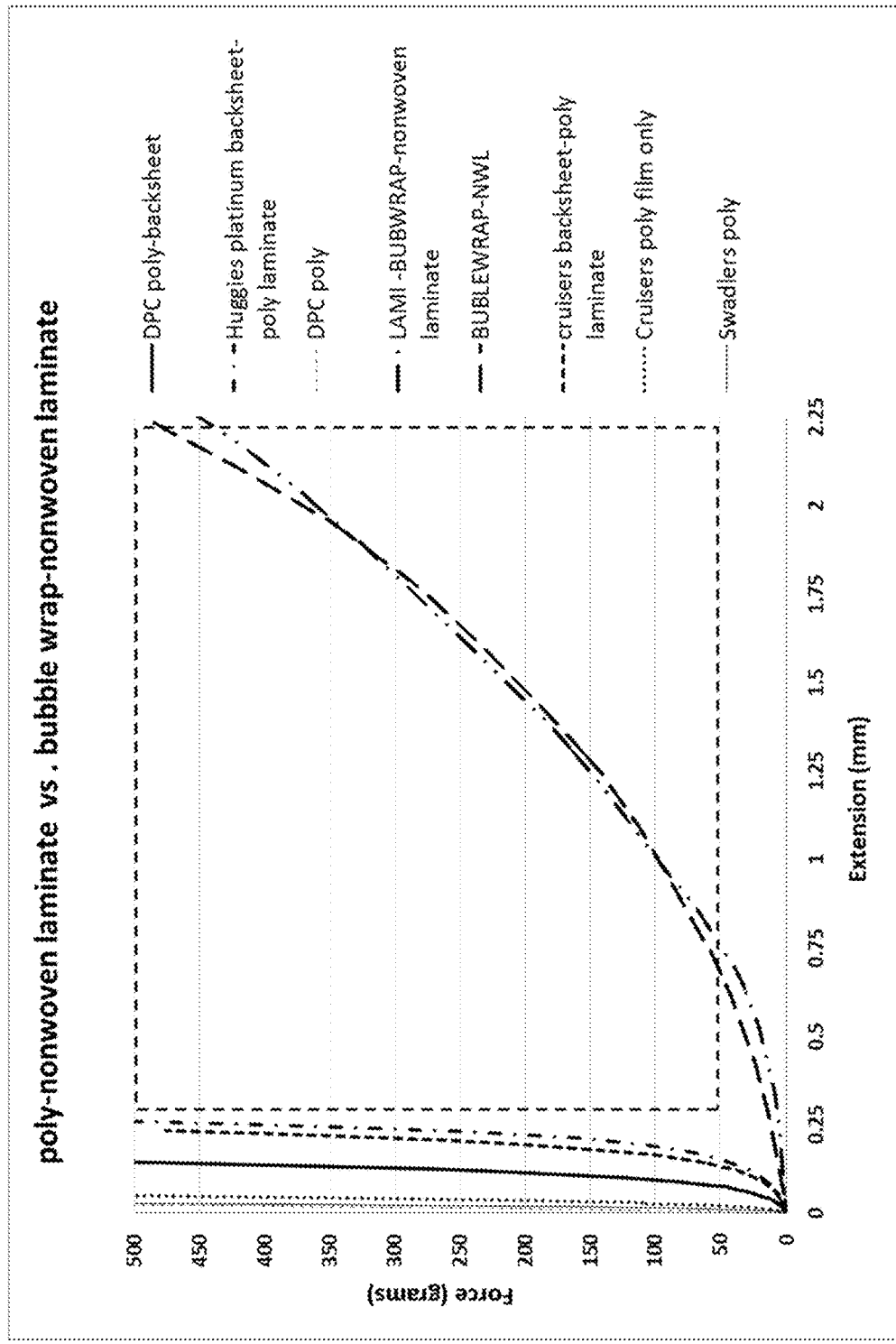

FIG. 14 shows a compression versus extension plot comparing existing DPC poly-backsheet laminate and bubble wrap/backsheet laminates. When the poly film with these bubbles is laminated to soft backsheet by hot melt, a region between the air pockets (dips) will not be bonded to the backsheet nonwoven. These areas between the air pockets will not restrict the backsheet nonwoven. As a result, these unbounded regions serve as the hinge point and provide additional drape to the backsheet-poly laminate of the absorbent article. Results showed that bubble wrap-backsheet laminates exhibited a higher cushioning or deformation than the current DPC poly-backsheet laminate configuration. Bubble wrap nonwoven laminates exhibited a deformation range of 0.25 mm to 2.25 mm under a compression range of 50 grams to 500 grams using the compression test described herein.

Figure 15A:
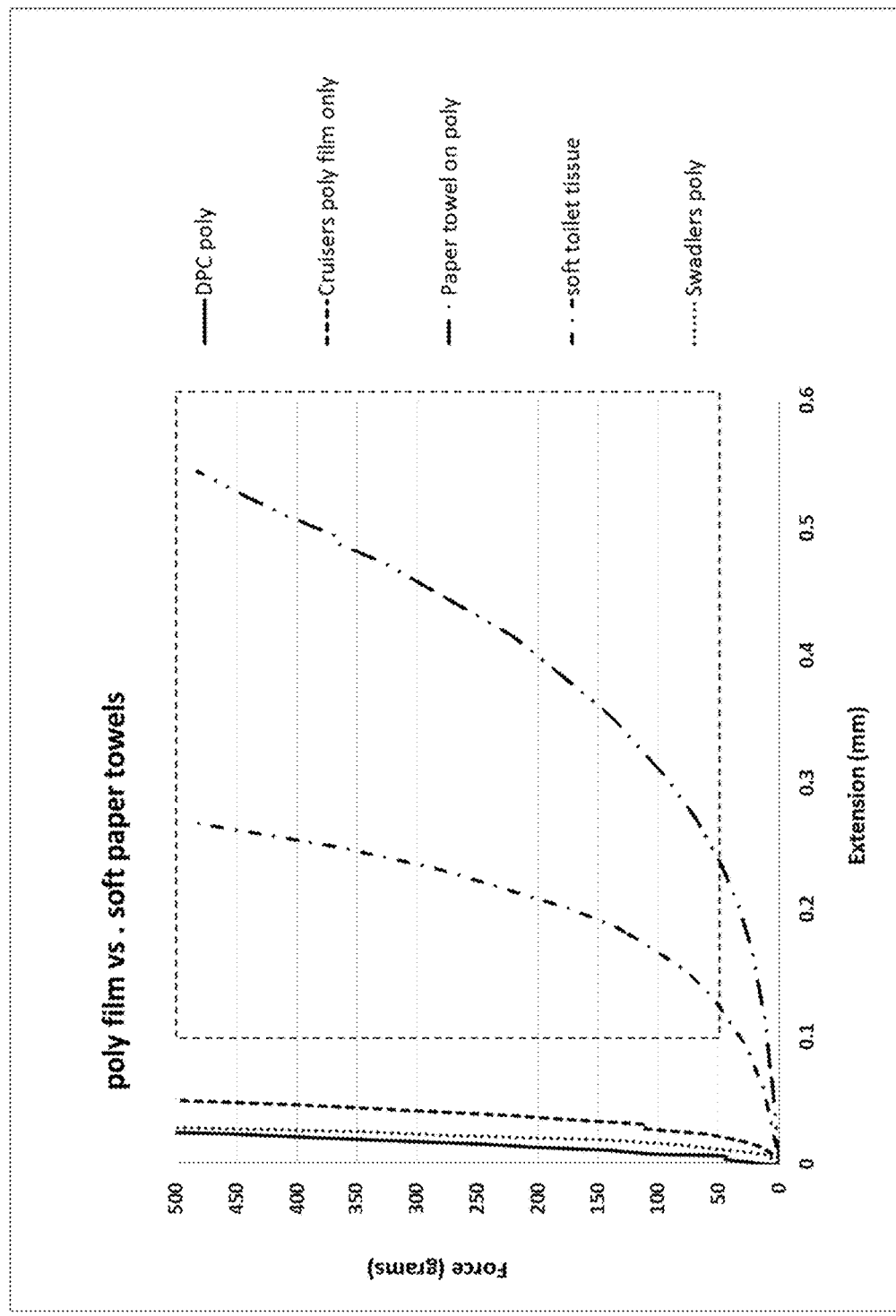

FIG. 15A shows a comparison between existing DPC poly film, Cruisers poly film, Swadlers poly film, and soft toilet tissue paper. DPC poly film is a 0.6 mil polypropylene poly film. Cruisers poly film is obtained from a commercially available Cruisers diaper product and Swadlers poly film is obtained from a commercially available Swadlers diaper product. Embossed paper towel and soft toilet tissue type materials were used as way to increase cushioning effect in the outer cover. Examples of soft toilet tissue include commercially available Charmin Ultra Soft toilet paper. Paper towel material is used in between the nonwoven backsheet and the polyfilm. Results showed that soft toilet tissue and asymmetric embossed paper towels exhibit a deformation range of 0.12 mm to 0.55 mm under a compression range of 50 grams to 500 grams using the compression test described herein.

Figure 15B:
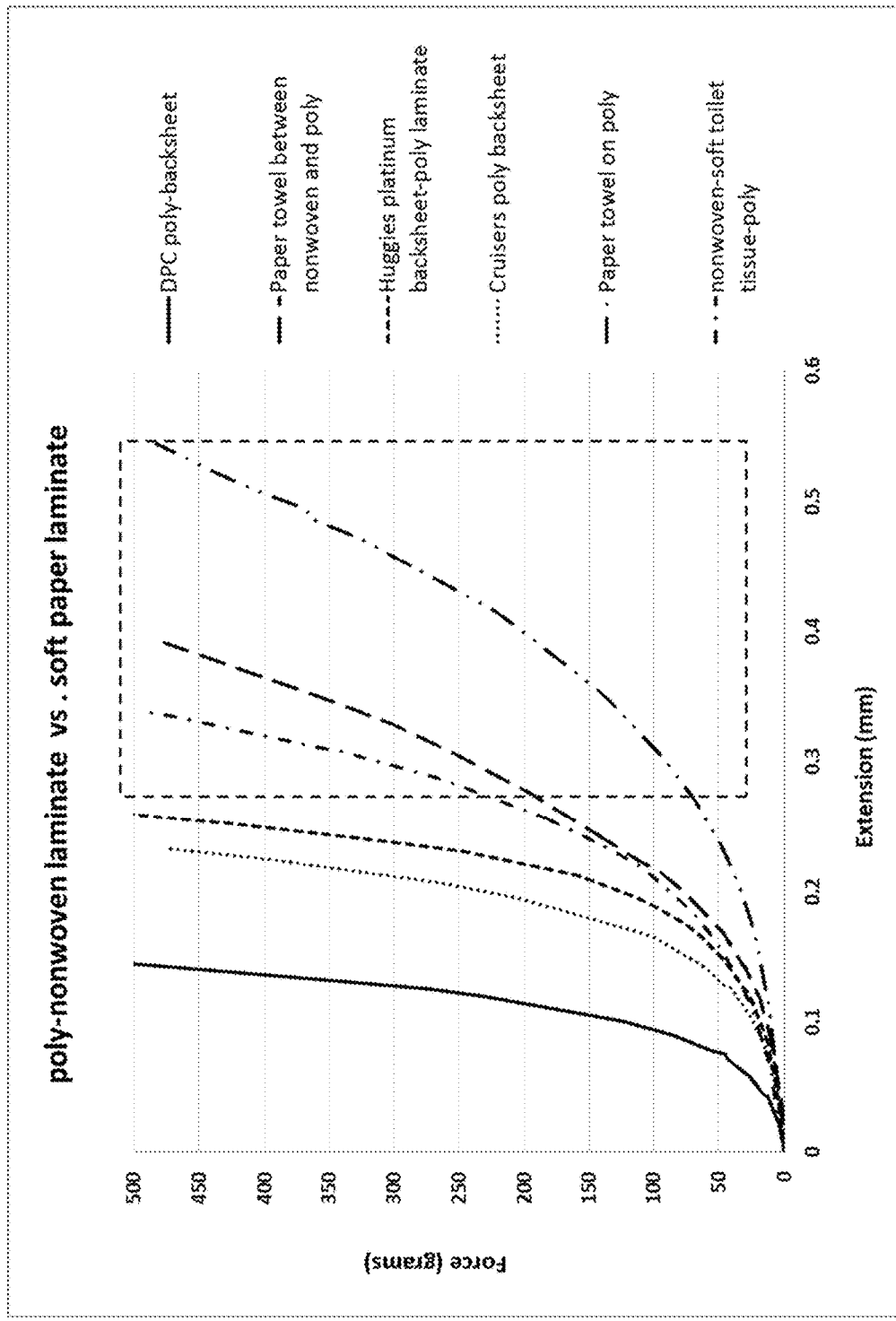

FIG. 15B shows a comparison between existing DPC poly-backsheet laminate, competitors' poly film, and a soft paper laminate. DPC poly-backsheet laminate is a laminate having 13.5 gsm PGI nonwoven and 0.6 mil polypropylene poly film. Results showed that soft toilet tissue and asymmetric embossed paper towels, when laminated between poly film and nonwoven backsheet, exhibit a deformation range of 0.2 mm to 0.5 mm under a compression range of 50 grams to 500 grams using the compression test described herein.

In paper towels, two layers of paper are combined with a thin layer of adhesive and embossed to form many tiny air pockets that rapidly attract moisture. Diamond shapes are pressed into the paper to give it a quilted pattern that holds water. The Charmin paper towel had lower initial thickness before load compared to Bounty. The number of layers, bonding method, embossing structure determines the extent of cushiness of the paper towel.

Various asymmetrically embossed paper towels can be used to increase the tactile and cushiness of outer laminates. Based on how the embossed paper towels are manufactured, their basis weight, the method of drying used, fiber type, and embossed rolls, the embossed paper towels exhibit different cushiness/softness and z-directional deformation. The commercially available asymmetrically embossed paper towels and toilet tissue papers used during compression testing were Charmin Ultra-Soft by P&G, KCC, P&G, and Walmart Stores Inc.

Figure 16:
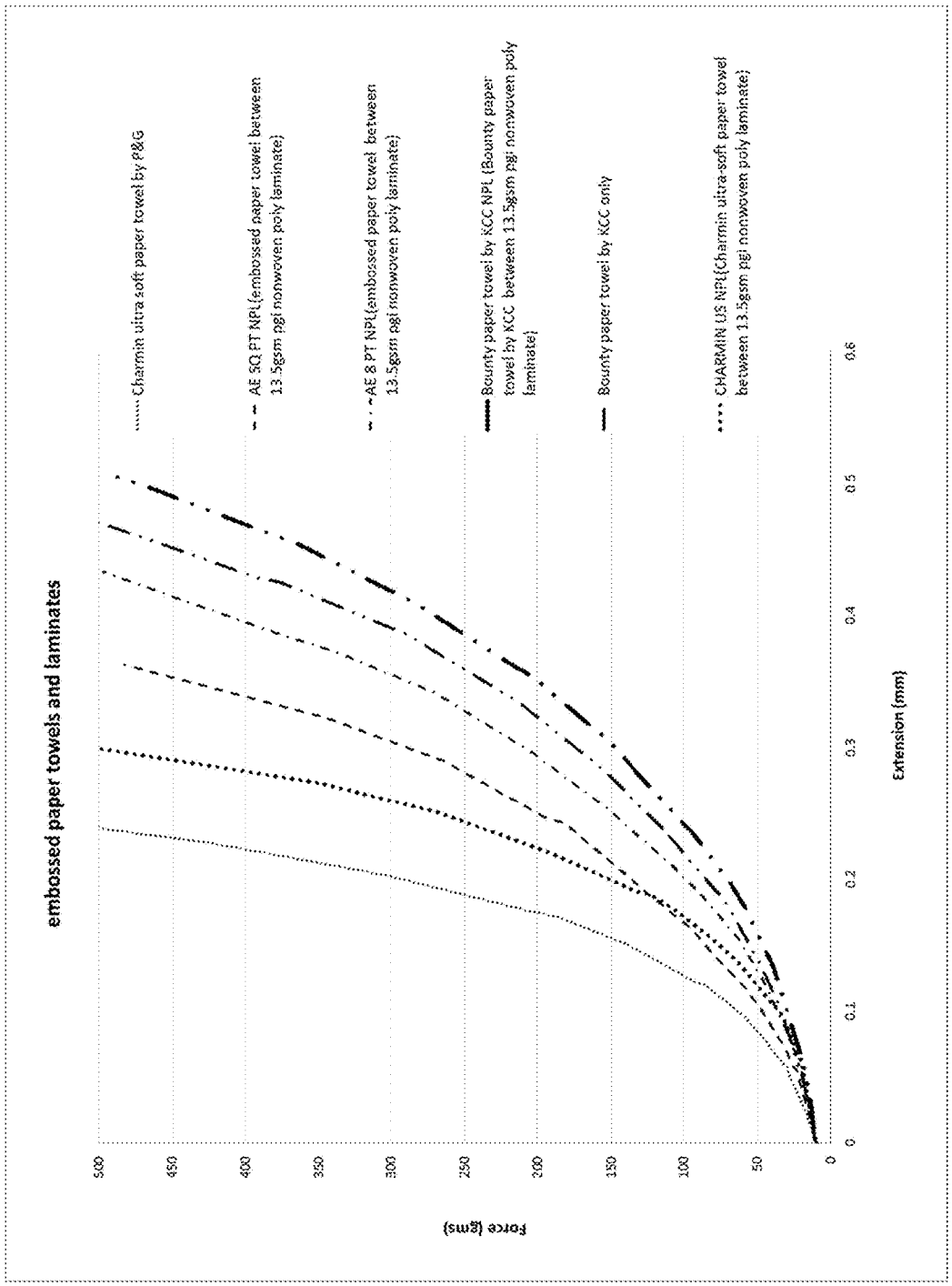

FIG. 16 and the table below show the cushiness/z-directional deformation exhibited by the different commercially available kitchen towels and their outer cover laminates. The table below displays measurements of a pre-load height of the sample material (HT-PL) and a height under an applied load of 500 grams (HT-LD). Among them, the kitchen towel Bounty distributed by KCC that had the maximum initial thickness or lofty paper towel formed the soft and cushion laminate and achieved maximum cushiness/z-directional deformation.

adhesive. Air pockets may be formed by increasing the distance between the spray/signature adhesive patterns by 10 mm or greater. Results showed a deformation range of 0.3 mm or higher under a compression force range of 50 grams to 500 grams using the compression test described herein.

Figure 19:
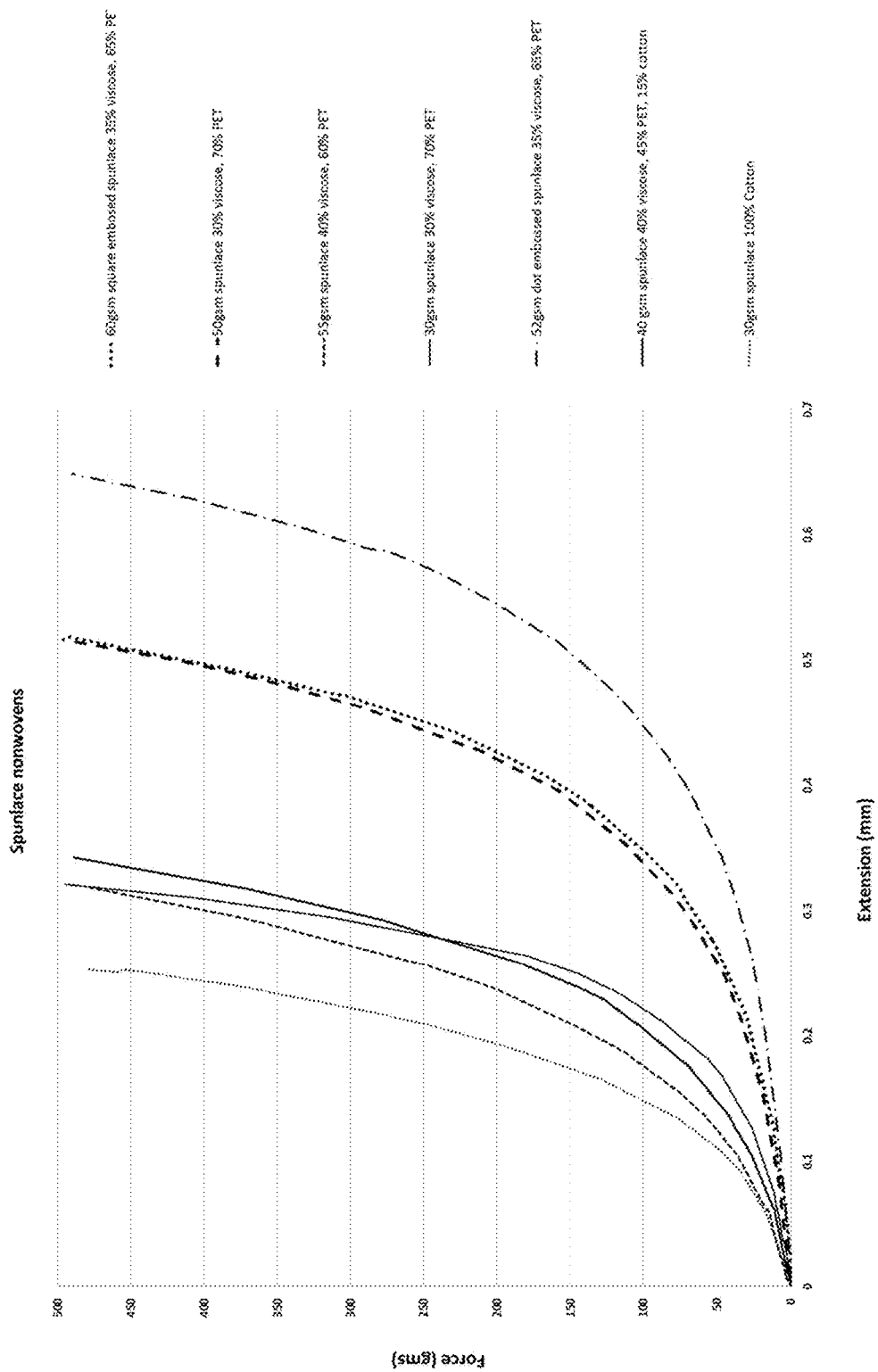

FIG. 19 shows a compression versus extension plot comparing spunlace nonwovens having various basis weights, fiber composition and embossed patterns. Results showed that spunlace soft nonwovens exhibit a deformation range of 0.1 mm to 0.6 mm under a compression range of 50 grams to 500 grams using the compression test described herein. Different basis weight, different embossed pattern, and different fiber composition has an impact on the extent of z-directional deformation exhibited by the spunlace nonwoven. Embossed spunlace nonwoven patterns exhibited more

| Sample | Material description | HT-PL (mm) | HT-LD (mm) |
|---|---|---|---|
| Charmin ultra-soft paper towel by P&G | commercially available Charmin ultra-soft paper towel by P&G | 0.44 | 0.2 |
| CHARMIN US NPL(Charmin ultra-soft paper towel between 13.5 gsm pgi nonwoven poly laminate) | commercially available Charmin ultra-soft paper towel between 13.5 gsm pgi nonwoven 0.6 mil polypropylene poly laminate | 0.61 | 0.31 |
| AE SQ PT NPL(embossed paper towel between 13.5 gsm pgi nonwoven poly laminate) | commercially available embossed paper towel type 1 between 13.5 gsm pgi nonwoven 0.6 mil polypropylene poly laminate | 0.62 | 0.26 |
| AE 8 PT NPL(embossed paper towel between 13.5 gsm pgi nonwoven poly laminate) | commercially available embossed paper towel type 2 between 13.5 gsm pgi nonwoven 0.6 mil polypropylene poly laminate | 0.68 | 0.25 |
| AE DOT PT NPL(embossed paper towel between 13.5 gsm pgi nonwoven poly laminate) | commercially available embossed paper towel type 3 between 13.5 gsm pgi nonwoven 0.6 mil polypropylene poly laminate | 0.73 | 0.27 |
| Bounty paper towel by KCC only | commercially available Bounty paper towel by KCC | 0.85 | 0.38 |
| Bounty paper towel by KCC NPL (Bounty paper towel by KCC between 13.5 gsm pgi nonwoven poly laminate) | commercially available Bounty paper towel by KCC between 13.5 gsm pgi nonwoven 0.6 mil polypropylene poly laminate | 0.98 | 0.47 |

Figure 17:
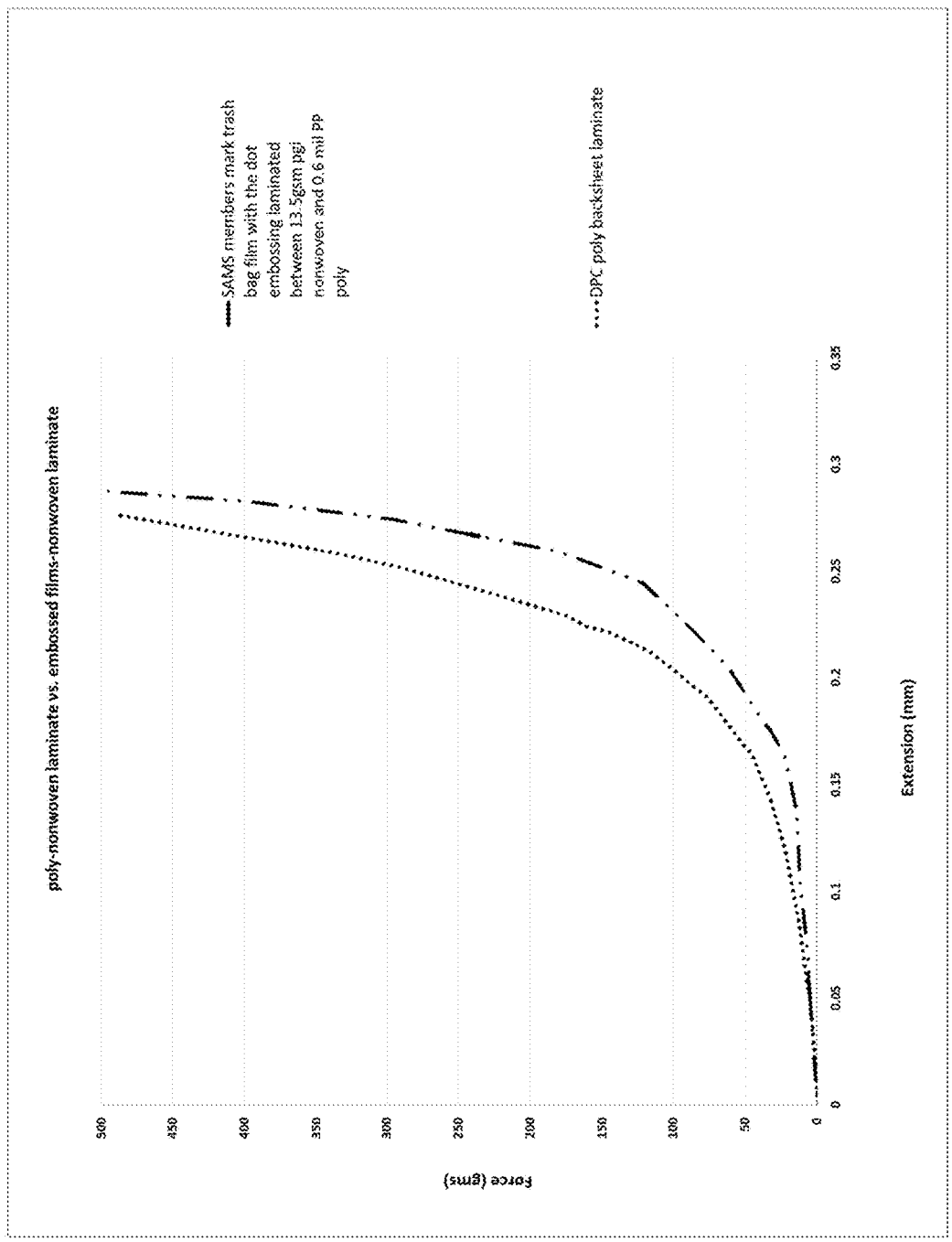

FIG. 17 shows a compression versus extension plot comparing an existing DPC poly film/backsheet laminate and a Sam's Member's Mark® bag in a 0.6 mil polypropylene poly film-13.5 gsm PGI nonwoven backsheet laminate. Poly film with a dot embossed pattern was obtained from a Member's Mark® trash bag, distributed by SAMS West Inc. Bentonville, Ark. The poly film with the dot embossing may be laminated between the poly film and nonwoven backsheet using an Elmer's® spray glue distributed by Elmer's Inc. Columbus Ohio Results showed a deformation range of 0.15 mm to 0.3 mm under a compression force range of 50 grams to 500 grams using the compression test described herein. Dimpled poly film exhibited directionally higher deformation but the deformation was not noticeably greater in the laminate samples having dimpled poly film.

Figure 18:
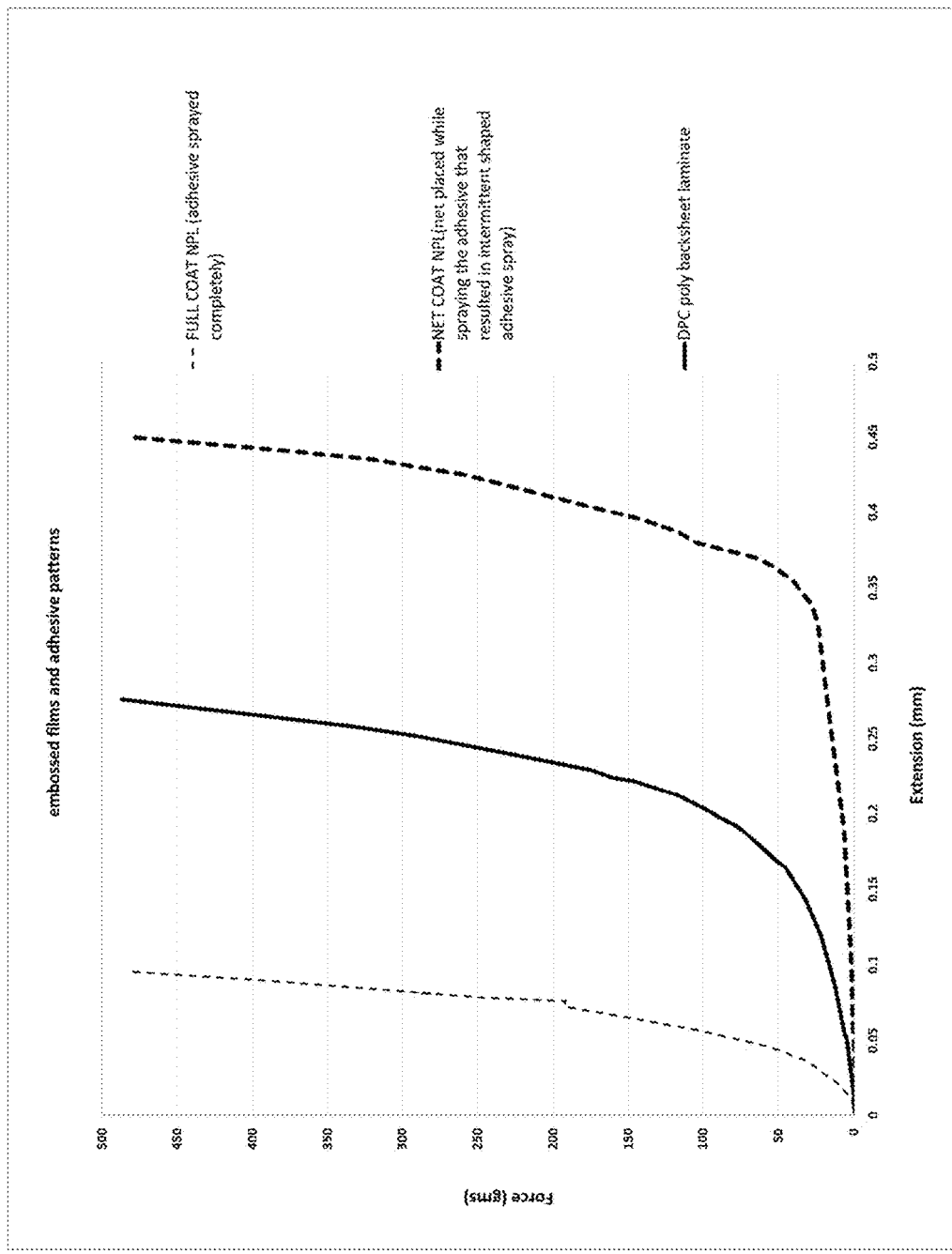

FIG. 18 shows a compression versus extension plot comparing an existing DPC poly film/backsheet laminate and various adhesive patterns. Distance between adhesive patterns was achieved by keeping net/mesh type films (e.g., 3 mm diameter mesh) on the poly films and spraying the z-direction deformation as compared to plain spunlace nonwovens. Also, the composition with 60% or higher PET fiber exhibited more z-directional deformation. Between the square embossed and dot embossed embodiments, the dot embossed spunlace exhibited more z-directional deformation. The dot or square embossed spunlace, when facing away from wearer towards outside, is more beneficial for bringing the tactile softness signal to the outer cover. When the user feels the outer cover they will be able to feel the embossed patterns.

The spunlace nonwovens listed in the table below were laminated between the 0.6 mil polypropylene poly film and a 13.5 gsm polypropylene soft nonwoven backsheet using an Elmer's multipurpose spray adhesive. The table below displays measurements of a pre-load height of the sample material (HT-PL) and a height under an applied compression load of 500 grams (HT-LD) using the compression test described herein.

| Sample | Material description | HT-PL (mm) | HT-LD (mm) |
|---|---|---|---|
| 60 gsm square embossed spunlace with 35% viscose, 65% PET | 60 gsm square embossed spunlace with 35% viscose, 65% PET | 0.81 | 0.29 |
| 50 gsm spunlace 30% viscose, 70% PET | 50 gsm spunlace 30% viscose, 70% PET | 0.77 | 0.25 |
| 55 gsm spunlace 40% viscose, 60% PET | 55 gsm spunlace 40% viscose, 60% PET | 0.63 | 0.31 |

| Sample | Material description | HT-PL (mm) | HT-LD (mm) |
|---|---|---|---|
| 30 gsm spunlace 30% viscose, 70% PET | 30 gsm spunlace 30% viscose, 70% PET | 0.46 | 0.14 |
| 52 gsm dot embossed spunlace 35% viscose, 65% PET | 52 gsm dot embossed spunlace 35% viscose, 65% PET | 0.92 | 0.27 |
| 40 gsm spunlace 40% viscose, 45% PET, 15% cotton | 40 gsm spunlace 40% viscose, 45% PET, 15% cotton | 0.58 | 0.24 |
| 30 gsm spunlace 100% Cotton | 30 gsm spunlace 100% Cotton | 0.43 | 0.17 |
| 50 gsm spunlace −30% viscose, 70% NPL (spunlace between 13.5 gsm pgi nonwoven poly laminate) | 50 gsm spunlace V30P70-between 13.5 gsm pgi nonwoven and 0.6 mil polypropylene poly laminate | 0.96 | 0.42 |
| 30 gsm spunlace 100% Cotton-SPUNTECH NPL (spunlace between 13.5 gsm pgi nonwoven poly laminate) | 30 gsm spunlace 100% Cotton between 13.5 gsm pgi nonwoven and 0.6 mil polypropylene poly laminate | 0.63 | 0.32 |
| 40 gsm spunlace 40% viscose, 45% PET, 15% cotton-NPL(spunlace between 13.5 gsm pgi nonwoven poly laminate) | 40 gsm spunlace 40% viscose, 45% PET, 15% cotton between 13.5 gsm pgi nonwoven 0.6 mil polypropylene poly laminate | 0.84 | 0.39 |
| 52 gsm spunlace 35% viscose, 65% PET-NPL(spunlace between 13.5 gsm pgi nonwoven poly laminate) | 52 gsm spunlace 35% viscose, 65% PET-NPL between 13.5 gsm pgi nonwoven 0.6 mil polypropylene poly laminate | 0.92 | 0.27 |
| 55 gsm spunlace −40% viscose, 60% PET NPL (spunlace between 13.5 gsm pgi nonwoven poly laminate) | 55 gsm spunlace −40% viscose, 60% PET between 13.5 gsm pgi nonwoven 0.6 mil polypropylene poly laminate | 0.99 | 0.48 |
| 60 gsm square embossed spunlace 35% viscose, 65% PET NPL(spunlace between 13.5 gsm pgi nonwoven poly laminate) | 60 gsm square embossed spunlace 35% viscose, 65% PET between 13.5 gsm pgi nonwoven and 0.6 mil polypropylene poly laminate | 1.11 | 0.44 |
| 50 gsm spunlace 30% viscose, 70% PET-NPL(spunlace between 13.5 gsm pgi nonwoven poly laminate) | 50 gsm spunlace 30% viscose, 70% PET-between 13.5 gsm pgi nonwoven and 0.6 mil polypropylene poly laminate | 1.06 | 0.41 |

Figure 20:
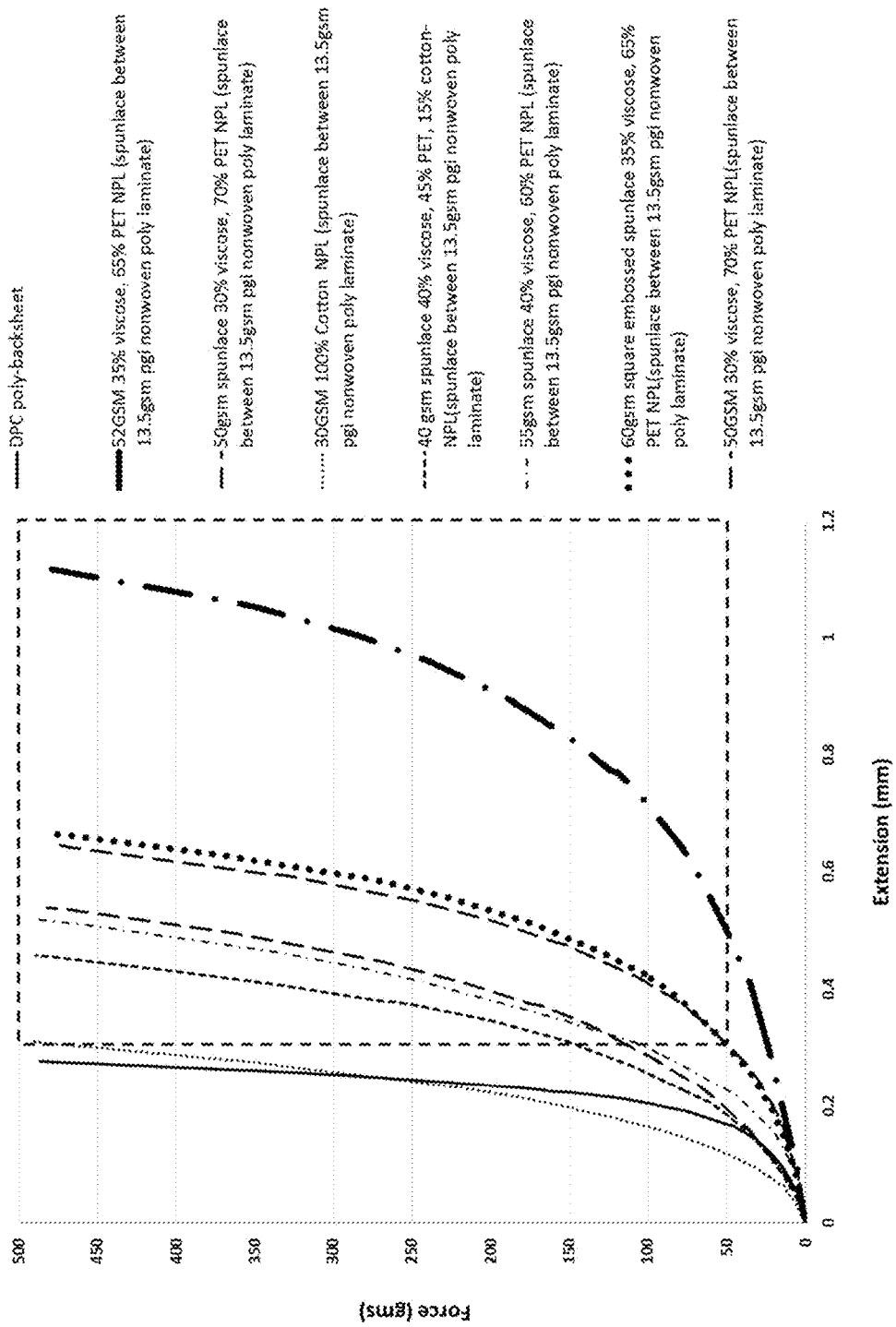

Laminates were also tested for cushiness and the compression versus extension plot is shown in FIG. 20. Results showed that the laminates exhibited a deformation range of 0.18 mm to 1.2 mm under a compression force range of 50 to 500 grams using the compression test described herein. Similar to the spunlace nonwovens based on the data, the samples with 60% or more PET fiber blend are preferred. 100% natural fibers in above case cotton fibers did not exhibit much of the cushiness. Spunlace nonwovens mentioned here could be commercially sourced from Spuntech Industries Inc., Jacob Holmes, or Berry plastics.

Figure 21:
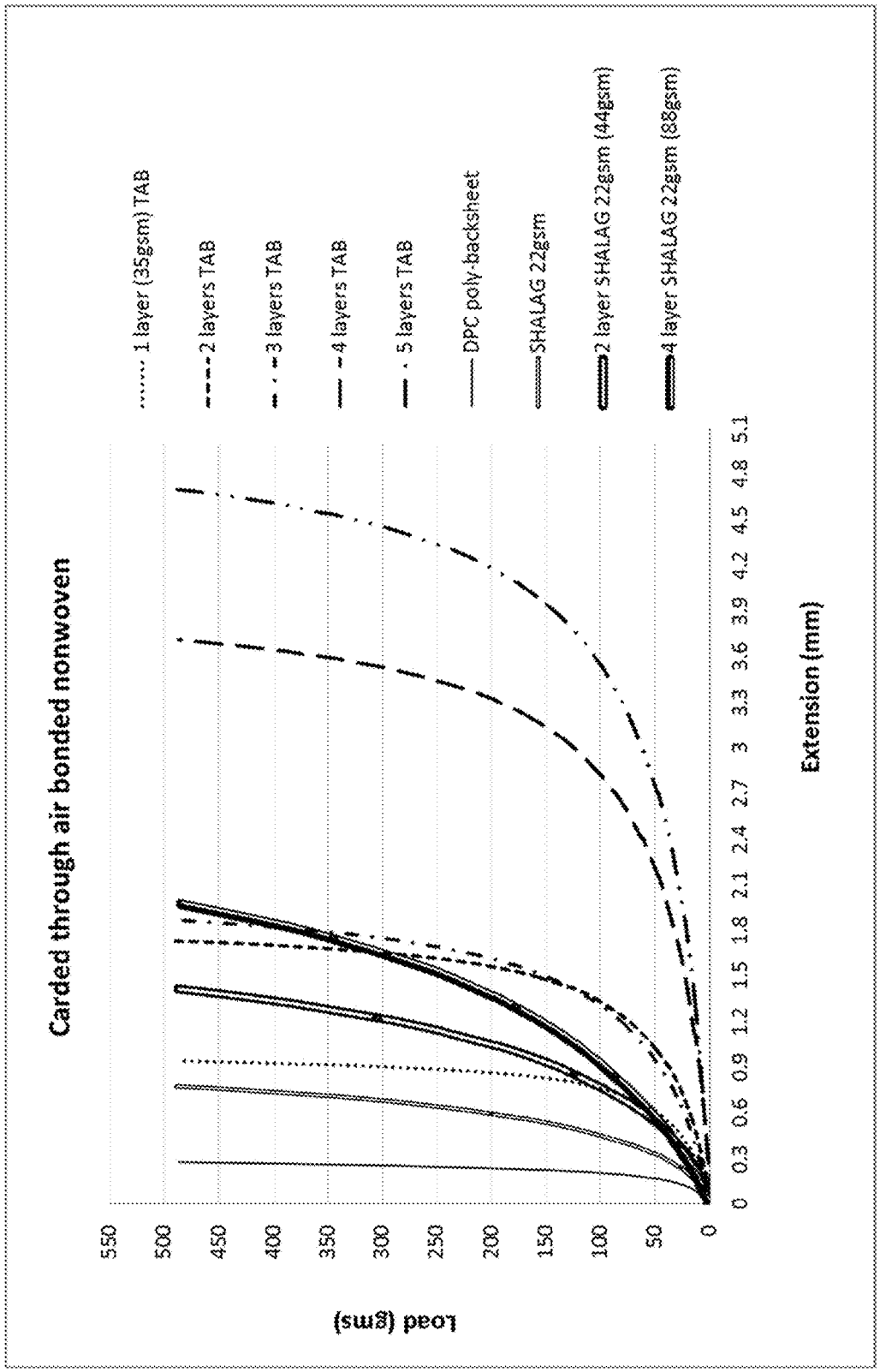

FIG. 21 shows a compression versus extension plot comparing an existing DPC poly film-backsheet laminate with carded and through-air bonded laminates having various numbers of layers.

| Sample | Material description | HT-PL (mm) | HT-LD (mm) |
|---|---|---|---|
| 1 layer TAB (35 gsm) | 1 layer of Texsus 35 gsm PET/PE carded, through-air bonded nonwoven | 1.09 | 0.15 |
| 2 layer TAB (70 gsm) | 2 layer of 35 gsm PET/PE carded, through-air bonded nonwoven, total 70 gsm | 2.1 | 0.37 |
| 3 layer TAB (105 gsm) | 3 layer of 35 gsm PET/PE carded, through-air bonded nonwoven, total 105 gsm | 2.47 | 0.6 |
| 4 layer TAB (140 gsm) | 4 layer of 35 gsm PET/PE carded, through-air bonded nonwoven, total 140 gsm | 4.59 | 0.88 |
| 5 layer TAB (175 gsm) | 5 layer of 35 gsm PET/PE carded, through-air bonded nonwoven, total 175 gsm | 5.85 | 1.15 |
| SHALAG 22 gsm | 1 layer of Shalag 22 gsm PP/PE carded, through-air bonded nonwoven | 1.1 | 0.33 |
| 2 layer | 2 layer of Shalag 22 gsm PP/PE | 2.22 | 0.81 |
| SHALAG 22 gsm (44 gsm) | carded, through-air bonded nonwoven total 44 gsm | | |
| 4 layer | 4 layer of Shalag 22 gsm PP/PE | 3.55 | 1.58 |
| SHALAG 22 gsm (88 gsm) | carded, through-air bonded nonwoven total 88 gsm | | |

Carded and through air bonded nonwovens can be obtained from commercial nonwoven manufacturers like Shalag—Oxford, N.C., Texsus—Italy, Freudenberg, Berry plastics. Carded and through air bonded nonwovens exhibited a deformation range of 0.4 mm or higher under a compression force range of 50 grams to 500 grams using the compression test described herein. The basis weight of carded and TAB nonwoven can be 22 gsm or higher with fiber composition made of 100% polyester, 100% PP, bi-component fibers of PP/PE, PET/PE, PET/co-PET, PP/PET, blend of all these or selection of these fibers or blend of these fibers along with other natural fibers like cotton, bleached cotton, unbleached cotton, jute, ramie, flax, and the like.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A disposable absorbent article comprising:
   an absorbent structure; and
   a laminate comprising:
     a layer of a nonwoven fabric; and
     a layer of cushion material defining a plurality of air pockets between opposing first and second surfaces of the cushion material such that the first surface defines hills, the first surface facing the nonwoven fabric;
     where the laminate has an uncompressed thickness of between 0.4 millimeters and 8.5 millimeters, and a thickness of between 0.1 millimeters and 5.0 millimeters when subjected to a compressive force of 500 grams;
   where the laminate is positioned such that the cushion material is disposed between the nonwoven fabric and the absorbent structure and the nonwoven fabric defines an outer surface of the absorbent article.

2. The article of claim 1, where the laminate comprises a layer of film such that the layer of film and the layer of cushion material are both disposed between the nonwoven fabric and the absorbent structure.

3. The article of claim 1, where the laminate includes a z-direction deformation in the range of about 0.12 millimeters to 2.5 millimeters under a compressive force in the range of 50 to 500 grams.

4. The article of claim 1, where the absorbent structure includes a superabsorbent polymeric (SAP) particulate material.

5. The article of claim 4, where the absorbent structure includes cellulose fiber.

6. The article of claim 1, where the layer of cushion material includes first and second films defining the plurality of air pockets, the first film defining the first surface of the cushion material and the second film defining the second surface of the cushion material.

7. The article of claim 6, where:
   at least one of the films is at least partially dimpled, pleated, or embossed; and
   the cushion material is configured to exhibit a deformation in the range of 0.15 mm to 0.3 mm under a compression force in the range of 50 grams to 500 grams.

8. The article of claim 6, where the first and second films are laminated to each other adhesively, thermally, by co-extrusion, ultrasonically, or any combination thereof.

9. The article of claim 1, further comprising a spray or signature in an adhesive pattern with at least one spacing of 10 mm or larger such that the laminate is configured to exhibit a deformation in the range of 0.3 mm or more under a compressive force in the range of 50 grams to 500 grams.

10. The article of claim 1, where the layer of cushion material includes a spunlace nonwoven defining the plurality of air pockets such that the laminate is configured to exhibit a deformation in the range of 0.18 mm to 1.2 mm under a compressive force in the range of 50 grams to 500 grams.

11. The article of claim 10, where the spunlace nonwoven include fibers with 60% or more of a polyethylene terephthalate (PET) fiber blend.

12. The article of claim 1, where the layer of cushion material includes a spunlace nonwoven having an embossed pattern facing away from the absorbent structure to define the plurality of air pockets.

13. The article of claim 1, where the layer of cushion material includes a carded through-air bonded (TAB) nonwoven defining the plurality of air pockets and covering at least the absorbent structure, such that the laminate is configured to exhibit a deformation in the range of 0.4 mm or more under a compressive force in the range of 50 grams to 500 grams.

14. The article of claim 13, where a basis weight of the carded TAB nonwoven is 22 gsm or higher with a fiber composition including any combination of the following: polyester, polypropylene (PP), bi-component fibers of PP-polyethylene (PE), polyethylene terephthalate (PET)-PE, PET/co-extruded polyethylene terephthalate (co-PET), PP-PET, cotton, bleached cotton, unbleached cotton, jute, ramie, and flax.

15. The article of claim 1, where the layer of cushion material includes at least one material selected from the group consisting of: closed-cell polymeric foam, open-cell polymeric foam, bubble wrap, and embossed paper.

16. The article of claim 1, where the layer of cushion material is resilient.

17. The article of claim 1, where the cushion material is laminated to the nonwoven fabric.

18. The article of claim 17, where the first surface of the cushion material has one or more regions, each of which is disposed between at least two of the hills and is not bonded to the nonwoven fabric.

19. A method of assembling an absorbent article, the method comprising:
   laminating a layer of cushion material and a layer of a nonwoven fabric to form a laminate, the layer of cushion material defining a plurality of air pockets between first and second surfaces of the cushion material such that the first surface defines hills, the first surface facing the nonwoven fabric; and
   positioning the laminate on an absorbent structure such that the cushion material is disposed between the nonwoven fabric and the absorbent structure and the nonwoven fabric defines an outer surface of the absorbent article;
   where the laminate has an uncompressed thickness of between 0.4 millimeters and 8.5 millimeters, and a thickness of between 0.1 millimeters and 5.0 millimeters when subjected to a compressive force of 500 grams.

20. The method of claim 19, where the absorbent structure includes a superabsorbent polymeric (SAP) particulate material.

21. The method of claim 19, where laminating the layer of cushion material and the layer of nonwoven fabric includes at least one joining process selected from the group consisting of: thermal bonding, ultrasonic bonding, adhesive lamination, pressure lamination, and co-extrusion.

22. The method of claim 19, where the layer of cushion material includes at least one material selected from the group consisting of: closed-cell polymeric foam, open-cell polymeric foam, bubble wrap, and embossed paper.

23. The method of claim 22, where the layer of cushion material includes at least one of the open-cell polymeric foam and the embossed paper and the method comprises bonding a liquid-impervious polymeric film to the cushion material.

24. The method of claim 19, where the layer of cushion material includes a carded and through-air bonded nonwoven layer with a basis weight of 20 gsm or higher.

25. The method of claim 19, where the positioning is performed such that the cushion material covers the absorbent structure.

26. The method of claim 19, where:
the first surface of the cushion material has one or more regions, each of which is disposed between at least two of the hills; and
laminating is performed such that the cushion material is laminated to the nonwoven fabric and the region(s) of the cushion material are not bonded to the nonwoven fabric.

27. A disposable absorbent article, comprising:
an absorbent structure; and
a layer of cushion material coupled to the absorbent structure such that the layer of cushion material defines an outer surface of the absorbent article, the layer of cushion material defining a plurality of air pockets;
where the layer of cushion material has an uncompressed thickness of between 0.4 millimeters and 8.5 millimeters, and a thickness of between 0.1 millimeters and 5.0 millimeters when subjected to a compressive force of 500 grams; and
where the layer of cushion material includes at least one material selected from the group consisting of: closed-cell polymeric foam, open-cell polymeric foam, bubble wrap, and embossed paper.

\* \* \* \* \*